(12) United States Patent
Nesarikar et al.

(10) Patent No.: US 11,741,562 B2
(45) Date of Patent: Aug. 29, 2023

(54) REMOTE MONITORING WITH ARTIFICIAL INTELLIGENCE AND AWARENESS MACHINES

(71) Applicants: Abhijit R. Nesarikar, Plano, TX (US); Ashlesha A. Nesarikar, Plano, TX (US); Anika A. Nesarikar, Plano, TX (US)

(72) Inventors: Abhijit R. Nesarikar, Plano, TX (US); Ashlesha A. Nesarikar, Plano, TX (US); Anika A. Nesarikar, Plano, TX (US)

(73) Assignee: Shalaka A. Nesarikar, Plano, TX (US)

( * ) Notice: Subject to any disclaimer, the term of this patent is extended or adjusted under 35 U.S.C. 154(b) by 0 days.

(21) Appl. No.: 17/906,844

(22) PCT Filed: Jun. 12, 2021

(86) PCT No.: PCT/IB2021/055193
§ 371 (c)(1),
(2) Date: Sep. 20, 2022

(87) PCT Pub. No.: WO2021/255610
PCT Pub. Date: Dec. 23, 2021

(65) Prior Publication Data
US 2023/0118182 A1      Apr. 20, 2023

Related U.S. Application Data

(60) Provisional application No. 62/705,296, filed on Jun. 19, 2020.

(51) Int. Cl.
*G06Q 50/26* (2012.01)
*G16H 40/20* (2018.01)
(Continued)

(52) U.S. Cl.
CPC ............. *G06Q 50/26* (2013.01); *G06N 20/00* (2019.01); *G16H 20/00* (2018.01); *G16H 40/20* (2018.01); *G16H 40/67* (2018.01); *G16H 50/80* (2018.01)

(58) Field of Classification Search
CPC ........ G16H 40/67; G16H 40/20; G16H 50/80; G06N 20/00
(Continued)

(56) References Cited

U.S. PATENT DOCUMENTS

| | | |
|---|---|---|
| 8,626,700 B1 | 1/2014 | Monraz et al. |
| 9,414,198 B2 | 8/2016 | Forstall et al. |

(Continued)

FOREIGN PATENT DOCUMENTS

| | | |
|---|---|---|
| CN | 107067274 A | 8/2017 |

OTHER PUBLICATIONS

Albus, James S. "4-D/RCS: A Reference Model Architecture for Demo III"; National Institute of Standards and Technology, Gaithersburg, MD (1997). May have been otherwise available before 1997.
(Continued)

*Primary Examiner* — Michael Tomaszewski

(57) ABSTRACT

Systems and methods for awareness machines and artificial intelligence (AI) based community wide care that may monitor one or more event in one or more domain are described. In an embodiment, a community wide care may monitor one or more event in real-time. In another embodiment, a multifaceted community wide care may enhance intelligence and awareness regarding one or more event. A functional performance measure (FPM) is described for the community wide care and the multifaceted community wide care. In an embodiment, one or more FPM for a community wide care may be evaluated to analyze performance and viability of the community wide care. The one or more FPM
(Continued)

may be formulated with one or more metric, which may be computed to derive one or more performance indicator for the community wide care.

47 Claims, 6 Drawing Sheets

(51) Int. Cl.
  *G06N 20/00* (2019.01)
  *G16H 20/00* (2018.01)
  *G16H 40/67* (2018.01)
  *G16H 50/80* (2018.01)

(58) Field of Classification Search
  USPC .......................................................... 705/2–3
  See application file for complete search history.

(56) References Cited

U.S. PATENT DOCUMENTS

| | | | |
|---|---|---|---|
| 9,456,298 B2 | 9/2016 | Lee et al. | |
| 9,495,307 B2 | 11/2016 | Zadesky et al. | |
| 9,514,642 B2 | 12/2016 | Lotz et al. | |
| 9,578,602 B1 | 2/2017 | Acharya et al. | |
| 9,578,621 B2 | 2/2017 | Forstall et al. | |
| 10,388,152 B2 | 8/2019 | Biehle et al. | |
| 10,839,302 B2 | 11/2020 | Wright et al. | |
| 2003/0163351 A1* | 8/2003 | Brown | G16H 70/60 600/300 |
| 2004/0008125 A1* | 1/2004 | Aratow | G08B 31/00 340/870.07 |
| 2005/0055330 A1* | 3/2005 | Britton | H04L 67/01 |
| 2005/0105765 A1 | 5/2005 | Han et al. | |
| 2006/0007308 A1 | 1/2006 | Ide et al. | |
| 2007/0021879 A1 | 1/2007 | DelNero et al. | |
| 2007/0021880 A1 | 1/2007 | Appleby et al. | |
| 2007/0291118 A1 | 12/2007 | Shu et al. | |
| 2009/0137881 A1* | 5/2009 | Ebert | G16H 50/80 600/300 |
| 2009/0174573 A1 | 7/2009 | Smith | |
| 2009/0177495 A1* | 7/2009 | Abousy | G16H 40/67 705/3 |
| 2009/0216747 A1* | 8/2009 | Li | G06Q 10/067 707/999.005 |
| 2009/0216860 A1* | 8/2009 | Li | G06F 16/9566 709/219 |
| 2009/0319295 A1* | 12/2009 | Kass-Hout | G16H 50/80 707/999.102 |
| 2012/0090010 A1 | 4/2012 | Dace et al. | |
| 2012/0218412 A1 | 8/2012 | Dellantoni et al. | |
| 2013/0238356 A1* | 9/2013 | Torii | G06Q 10/10 705/2 |
| 2014/0320666 A1 | 10/2014 | Badawy et al. | |
| 2015/0179062 A1 | 6/2015 | Ralston et al. | |
| 2015/0238692 A1* | 8/2015 | Peterson | A61N 1/046 604/503 |
| 2016/0210559 A1* | 7/2016 | Jean-Baptiste | G16H 50/80 |
| 2016/0240055 A1 | 8/2016 | Donovan et al. | |
| 2016/0253883 A1 | 9/2016 | Westmacott et al. | |
| 2016/0254854 A1 | 9/2016 | Wharton et al. | |
| 2016/0264045 A1 | 9/2016 | Ng-Thow-Hing et al. | |
| 2016/0269378 A1 | 9/2016 | Ye | |
| 2016/0347329 A1 | 12/2016 | Zelman et al. | |
| 2017/0011131 A1* | 1/2017 | Li | G06F 16/9566 |
| 2017/0050642 A1 | 2/2017 | Heckmann et al. | |
| 2017/0148291 A1 | 5/2017 | Barnwal | |
| 2018/0136000 A1 | 5/2018 | Rasmusson et al. | |
| 2018/0190111 A1 | 7/2018 | Green et al. | |
| 2018/0225964 A1 | 8/2018 | Degani et al. | |
| 2018/0247527 A1 | 8/2018 | Biehle et al. | |
| 2019/0172590 A1* | 6/2019 | Vesto | G16H 50/50 |
| 2021/0107504 A1 | 4/2021 | Shtrom | |
| 2021/0150399 A1 | 5/2021 | Wright et al. | |
| 2021/0398236 A1* | 12/2021 | Nesarikar | G06N 20/00 |

OTHER PUBLICATIONS

Dot, US. "Preparing for the future of transportation: Automated vehicles 3.0." US https://www.transportation.gov/av/3 (2018). May have been otherwise available before 2018.
Initial Publication with ISR (A1 51/2021) for PCT Publication No. WO2021255610 dated Dec. 23, 2021, 69 pages (WO2021255610-PAMPH-20211223-6866.pdf).
Search Strategy for PCT Publication No. WO2021255610 dated Dec. 23, 2021, 6 pages (WO2021255610-SRSTR-20211223-4119.pdf).
(ISA/210) International Search Report for PCT Publication No. WO2021255610 dated Dec. 23, 2021, 2 pages. (WO2021255610-ISR-20211223-4117.pdf).
(ISA/237) Written Opinion of the International Searching Authority for PCT Publication No. WO2021255610 dated Dec. 23, 2021, 8 pages. (WO2021255610-WOSA-20211223-4120.pdf).
Informal Comments by Applicant on WO-ISA for PCT Publication No. WO2021255610 dated Dec. 23, 2021, 4 pages. (WO2021255610-WOSAC-20211223-4122.pdf).
"Intelligent Transport Systems (ITS); Vehicular Communications; Basic Set of Applications; Part 3: Specifications of Decentralized Environmental Notification Basic Service"; ETSI EN 302 637-3 V1.3.1 (Apr. 2019); 2019. May have been otherwise available before 2019.
"Intelligent Transport Systems (ITS); Vehicular Communications; Basic Set of Applications; Part 3: Specifications of Decentralized Environmental Notification Basic Service"; ETSI EN 302 637-3 V1.2.2 (Nov. 2014); 2014. May have been otherwise available before 2014.
"Intelligent Transport Systems (ITS); Vehicular Communications; Basic Set of Applications; Part 2: Specification of Cooperative Awareness Basic Service"; ETSI EN 302 637-2 V1.4.1 (Apr. 2019); 2019. May have been otherwise available before 2019.
"Intelligent Transport Systems (ITS); Vehicular Communications; Basic Set of Applications; Part 2: Specification of Cooperative Awareness Basic Service"; ETSI EN 302 637-2 V1.3.2 (2014-11); 2014. May have been otherwise available before 2014.
"Intelligent Transport Systems (ITS); Vehicular Communications; Basic Set of Applications; Definitions"; EISI TR 102 638 V1.1.1 (Jun. 2009); 2009. May have been otherwise available before 2009.
"Intelligent Transport Systems (ITS); Vehicular Communications; Basic Set of Applications; Part 3: Specifications of Decentralized Environmental Notification Basic Service"; ETSI TS 102 637-3 V1.1.1 (Sep. 2010); 2010. May have been otherwise available before 2010.
"Intelligent Transport Systems (ITS); Vehicular Communications; Basic Set of Applications; Part 2: Specification of Cooperative Awareness Basic Service"; ETSI TS 102 637-2 V1.2.1 (Mar. 2011); 2011. May have been otherwise available before 2011.
"Intelligent Transport Systems (ITS); Vehicular Communications; Basic Set of Applications; Part 2: Specification of Cooperative Awareness Basic Service"; ETSI TS 102 637-2 V1.1.1 (Apr. 2010); 2010. May have been otherwise available before 2010.
"Intelligent Transport Systems (ITS); Vehicular Communications; Basic Set of Applications; Part 1: Functional Requirements"; ETSI TS 102 637-1 V1.1.1 (Sep. 2010); 2010. May have been otherwise available before 2010.
"Intelligent Transport Systems (ITS); Users and applications requirements; Part 2: Applications and facilities layer common data dictionary; Release 2"; ETSI TS 102 894-2 V2.1.1 (Nov. 2022); 2022. May have been otherwise available before 2022.
"Intelligent Transport Systems (ITS); Users and applications requirements; Part 2: Applications and facilities layer common data dictionary"; ETSI TS 102 894-2 V1.3.1 (Aug. 2018); 2018. May have been otherwise available before 2018.
"Intelligent Transport Systems (ITS); Users and applications requirements; Part 2: Applications and facilities layer common data dictionary"; ETSI TS 102 894-2 V1.2.1 (Sep. 2014); 2014. May have been otherwise available before 2014.
"Intelligent Transport Systems (ITS); Users and applications requirements; Part 2: Applications and facilities layer common data dic-

(56) References Cited

OTHER PUBLICATIONS tionary"; ETSI TS 102 894-2 V1.1.1 (Aug. 2013); 2013. May have been otherwise available before 2013.
"Intelligent Transport Systems (ITS); Users and applications requirements; Part 1: Facility layer structure, functional requirements and specifications"; ETSI TS 102 894-1 V1.1.1 (Aug. 2013); 2013. May have been otherwise available before 2013.
SAE J2735_202211 V2X Communications Message Set Dictionary (Nov. 2022). May have been otherwise available before 2022.
SAE J2735_202007 V2X Communications Message Set Dictionary (Jul. 2020). May have been otherwise available before 2020.
SAE J2735_201603 Dedicated Short Range Communications (DSRC) Message Set Dictionary (Mar. 2016). May have been otherwise available before 2016.
Warneken et al.; "Helping and Cooperation at 14 Months of Age." Infancy 11(3) (2007): 271-294. May have been otherwise available before 2007.
Cassenti, Daniel N. Advances in Human Factors in Simulation and Modeling: Proceedings of the AHFE 2017 International Conference on Human Factors in Simulation and Modeling, Jul. 17-21, 2017, the Westin Bonaventure Hotel, Los Angeles, California, USA. vol. 591. Springer International Publishing AG, 2017. May have been otherwise available before 2017.
Cassenti, Daniel N. Advances in Human Factors in Simulation and Modeling☐: Proceedings of the AHFE 2018 International Conferences on Human Factors and Simulation and Digital Human Modeling and Applied Optimization, Held on Jul. 21-25, 2018, in Loews Sapphire Falls Resort at Universal Studios, Orlando, Florida, USA. Edited by Daniel N. Cassenti, 1st ed. 2019, vol. 780. Springer International Publishing, 2019. May have been otherwise available before 2018.
Cassenti, Daniel N. Advances in Human Factors and Simulation☐: Proceedings of the AHFE 2019 International Conference on Human Factors and Simulation, Jul. 24-28, 2019, Washington D.C., USA. Edited by Daniel N. Cassenti, 1st ed. 2020, vol. 958. Springer International Publishing, 2020. May have been otherwise available before 2019.
Cassenti, Daniel N. et al. Advances in Simulation and Digital Human Modeling☐: Proceedings of the AHFE 2020 Virtual Conferences on Human Factors and Simulation, and Digital Human Modeling and Applied Optimization, Jul. 16-20, 2020, USA. Edited by Daniel N. Cassenti et al., 1st ed. 2021, vol. 1206. Springer International Publishing, 2021. May have been otherwise available before 2020.
Wright, Julia L. et al. Advances in Simulation and Digital Human Modeling☐: Proceedings of the AHFE 2021 Virtual Conferences on Human Factors and Simulation, and Digital Human Modeling and Applied Optimization, Jul. 25-29, 2021, USA. Edited by Julia L. Wright et al., 1st ed. 2021, vol. 264. Springer International Publishing, 2021. May have been otherwise available before 2021.
ISO 37168, Smart community infrastructures—Guidance on smart transportation by electric Connected and Autonomous Vehicle (eCAV) and its application to on-demand responsive passenger services with shared vehicles. (Jun. 2022). May have been otherwise available before 2022.
ISO 37181, Smart community infrastructures—Smart transportation by autonomous vehicles on public roads. (Jun. 2022). May have been otherwise available before 2022.
Siciliano et al. "Springer Handbook of Robotics." Springer Nature, 2nd edition (2016). May have been otherwise available before 2016. [In three parts: Part one from p. 1 to 748, Part two from p. 749 to 1444, and Part three from p. 1445 to 2154.].
Sarter et al. "How in the world did we ever get into that mode? Mode error and awareness in supervisory control." Human Factors, 37.1 (1995), 5-19. May have been otherwise available before 1995.
Xie et al. "Situational assessments based on uncertainty-risk awareness in complex traffic scenarios." Sustainability 9.9 (Sep. 7, 2017): 1582. May have been otherwise available before 2017.
Salas et al. "Situational Awareness: Critical Essays on Human Factors in Aviation." Routledge (2016). (eBook published Oct. 24, 2017). May have been otherwise available before 2016. [In two parts: Part one from p. 1 to 283 and Part two from p. 284 to 545.].
IEEE Std 1872.2-2021, IEEE Standard for Autonomous Robotics (AuR) Ontology. (May 12, 2022). May have been otherwise available before 2022.
IEEE Std 1872-2015, IEEE Standard Ontologies for Robotics and Automation. (Apr. 10, 2015). May have been otherwise available before 2015.
IEEE Std 2846-2022, IEEE Standard for Assumptions in Safety-Related Models for Automated Driving Systems. (Apr. 22, 2022). May have been otherwise available before 2022.
IEEE Std 7001-2021, IEEE Standard for Transparency of Autonomous Systems. (Mar. 4, 2022). May have been otherwise available before 2022.
IEEE Std 7010-2020, IEEE Recommended Practice for Assessing the Impact of Autonomous and Intelligent Systems on Human Well-Being. (May 1, 2020). May have been otherwise available before 2020.
Koopman et al. "Proposed First Edition of the Standard for Safety for the Evaluation of Autonomous Products, UL 4600." https://archive.org/details/191213-ul-4600-voting-version (Uploaded by Phil Koopman Nov. 25, 2020). May have been otherwise available before 2020.
Koopman et al. "A safety standard approach for fully autonomous vehicles." (2019) https://users.ece.cmu.edu/~koopman/pubs/Koopman19_WAISE_UL4600.pdf May have been otherwise available before 2019.
Endsley et al. "Designing for Situation Awareness: An Approach to User-Centered Design." CRC Press, 2nd edition (2011). (eBook published Jan. 17, 2012). May have been otherwise available before 2011.
Stanton et al. "Human Factors Methods: A Practical Guide for Engineering and Design." CRC Press, 2nd edition (2013). (eBook published Jun. 11, 2017). May have been otherwise available before 2013.
SAE J3216_202005 Taxonomy and Definitions for Terms Related to Cooperative Driving Automation for On-Road Motor Vehicles (May 2020). May have been otherwise available before 2020.
SAE J3216_202107 Taxonomy and Definitions for Terms Related to Cooperative Driving Automation for On-Road Motor Vehicles (Jul. 2021). May have been otherwise available before 2021.
SAE J3016_201609 Taxonomy and Definitions for Terms Related to Driving Automation Systems for On-Road Motor Vehicles (Sep. 2016). May have been otherwise available before 2016.
SAE J3016_201806 Taxonomy and Definitions for Terms Related to Driving Automation Systems for On-Road Motor Vehicles (Jun. 2018). May have been otherwise available before 2018.
SAE J3016_202104 Taxonomy and Definitions for Terms Related to Driving Automation Systems for On-Road Motor Vehicles (Apr. 2021). May have been otherwise available before 2021.
Meyer and Beiker; "Road Vehicle Automation"; Springer International Publishing (2014). May have been otherwise available before 2014. See Parts II, III, and IV, etc.
Meyer and Beiker; "Road Vehicle Automation 2"; Springer International Publishing (2015). May have been otherwise available before 2015. See Parts II, III, IV, V, and VI, etc.
Meyer and Beiker; "Road Vehicle Automation 3"; Springer International Publishing (2016). May have been otherwise available before 2016. See Parts II, III, IV, and V, etc.
Meyer and Beiker; "Road Vehicle Automation 4"; Springer International Publishing (2018). May have been otherwise available before 2017. See Parts II, III, IV, and V, etc.
Meyer and Beiker; "Road Vehicle Automation 5"; Springer International Publishing (2019). May have been otherwise available before 2018. See Parts II, III, IV, and V, etc.
Meyer and Beiker; "Road Vehicle Automation 6"; Springer International Publishing (2019). May have been otherwise available before 2019. See Parts II, III, and IV, etc.
Meyer and Beiker; "Road Vehicle Automation 7"; Springer International Publishing (2020). May have been otherwise available before 2020. See Parts III, IV, and V, etc.
Van Rooji, Iris, et al. "Cognition and intractability: A guide to classical and parameterized complexity analysis." Cambridge Uni-

(56) References Cited

OTHER PUBLICATIONS versity Press, 2019. (https://doi.org/10.1017/9781107358331.001). May have been otherwise available before 2019.
McLeod et al., "Introduction to connectionist modelling of cognitive processes." New York, NY, US: Oxford University Press. (1998); xv 388.
Kremer, Stefan C. "Spatiotemporal Connectionist Networks: A Taxonomy and Review" Neural Computation 13 (2001): 249-306.
Sutton et al., "Reinforcement learning: An introduction." vol. 1, No. 1, Cambridge: MIT press, 1998. [In two parts: Part one from p. 1 to 246 and Part two from p. 247 to 551.].
Ratcliff, Roger. "Connectionist models of recognition memory: Constraints imposed by learning and forgetting functions." Psychological review 97.2 (1990): 285-308.
Nesarikar et al. "Phase transitions in random copolymers." The Journal of chemical physics 98.9 (1993): 7385-7397.
Nesarikar et al. "Liquid-liquid phase separation in linear low-density polyethylene." Journal of Polymer Science Part B: Polymer Physics 32.4 (1994): 641-646.
Clarke et al. "Human and Machine Learning in Non-Markovian Decision Making." PLoS One 10(4) (2015).
Metz, Cade; "Google Built Its Very Own Chips to Power Its AI Bots", Wired Business, May 18, 2016.
Chen et al. "The UCR Time Series Classification Archive." (2015). www.cs.ucr.edu/~eamonn/time_series_data/.
Reif, F. "Fundamentals of statistical and thermal physics." 1965, Ch. 1, pp. 1-41, McGraw-Hill Publishing Company.
StatLib; "StatLib—Datasets Archive", http://lib.stat.cmu.edu/datasets/.
Weiss et al., "Learning to predict extremely rare events" AAAI workshop on learning from imbalanced data sets (pp. 64-68). Austin: AAAI Press, 2000. May have been otherwise available before 2000.
Moussavi-Khalkhali et al., "Leveraging machine learning algorithms to perform online and offline highway traffic flow predictions." 2014 13th International Conference on Machine Learning and Applications (pp. 419-423). IEEE, 2014. May have been otherwise available before 2014.
Liu et al., "SSD: Single Shot MultiBox Detector." European Conference on Computer Vision (pp. 21-37). Springer, Cham, 2016. May have been otherwise available before 2016.
Fatima et al., "Survey of machine learning algorithms for disease diagnostic" Journal of Intelligent Learning Systems and Applications 9.01 (2017): 1. May have been otherwise available before 2017.
Balaji et al. "Urban traffic signal control using reinforcement learning agents." IET Intelligent Transport Systems 4.3 (2010): 177-188. May have been otherwise available before 2010.
Brown, Ronald. "Higher order symmetry of graphs." Irish Mathematical Society Bulletin, 1994. (https://citeseerx.ist.psu.edu/pdf/9a63962b6883f343da12b858c4d8f794986fc63f) May have been otherwise available before 1994.
Russell, Stuart. "Artificial Intelligence and the Problem of Control." 2022. (https://web.archive.org/web/20211216014732/http://link.springer.com/content/pdf/10.1007/978-3-030-86144-5_3.pdf) May have been otherwise available before 2022.
Liu et al. "Belief, Awareness, and Two-Dimensional Logic." International Joint Conference on Artificial Intelligence, 2003. (https://citeseerx.ist.psu.edu/pdf/48e5bf8eed21735b95395dfeb34c8f265ded5a15) May have been otherwise available before 2003.
Konolige, Kurt. "What awareness isn't: A sentential view of implicit and explicit belief." Proceedings of the 1986 Conference on Theoretical Aspects of Reasoning About Knowledge, 1986. (https://citeseerx.ist.psu.edu/doc/10.1.1.107.3114). May have been otherwise available before 1986.
Fagin et al. "Belief, awareness, and limited reasoning." Artificial Intelligence (pp. 39-76), 1988. (https://citeseerx.ist.psu.edu/pdf/047c4eec48260fe71f59ddcec5608d58cea4f7fe) May have been otherwise available before 1988.
Fagin et al. "Belief, Awareness, and Limited Reasoning: Preliminary Report." International Joint Conference on Artificial Intelligence, 1985. ( https://citeseerx.ist.psu.edu/pdf/c06648161a97d21ebcd733e28300e2e71f137ff5) May have been otherwise available before 1985.
Ren et al. "Faster R-CNN: Towards Real-Time Object Detection with Region Proposal Networks." (2016) arXiv e-prints. (https://arxiv.org/abs/1506.01497v3). May have been otherwise available before 2016.
"One DSP real time bid ad system based on blended learning model" 2017. Beijing Zhang Kuo Mobile Media Science And Technology Ltd (foreign patent CN107067274A, translation provided by USPTO communication).
Rasouli et al. "Autonomous Vehicles That Interact With Pedestrians: A Survey of Theory and Practice." (2018) arXiv e-prints. (https://arxiv.org/abs/1805.11773v1). May have been otherwise available before 2018.
Mahadevan et al. "Communicating Awareness and Intent in Autonomous Vehicle-Pedestrian Interaction." (2018) (https://www.researchgate.net/publication/324664147_Communicating_Awareness_and_Intent_in_Autonomous_Vehicle-Pedestrian_Interaction). May have been otherwise available before 2018.
Nguyen et al. "Designing for Projection-based Communication between Autonomous Vehicles and Pedestrians." (2019) (http://www.medien.ifi.lmu.de/pubdb/publications/pub/hollaender2019AutoUI-2/hollaender2019AutoUI-2.pdf) Retrieved from (https://web.archive.org/web/20221024072548/http://www.medien.ifi.lmu.de/pubdb/publications/pub/hollaender2019AutoUI-2/hollaender2019AutoUI-2.pdf). May have been otherwise available before 2019.
Butt et al. "On the integration of enabling wireless technologies and sensor fusion for next-generation connected and autonomous vehicles." IEEE Access 10 (2022): 14643-14668 (https://ieeexplore.ieee.org/stamp/stamp.jsp?arnumber=9690855). May have been otherwise available before 2022.
Eisma et al. "External human-machine interfaces: Effects of message perspective." (2021) Transportation research part F, 78, 30-41 (https://www.sciencedirect.com/science/article/pii/S1369847821000206?via%3Dihub).May have been otherwise available before 2021.
Schneider et al. "Increasing the User Experience in Autonomous Driving through different Feedback Modalities." (2021) (https://www.researchgate.net/publication/350858958_Increasing_the_User_Experience_in_Autonomous_Driving_through_different_Feedback_Modalities). May have been otherwise available before 2021.
Faas et al. "A Longitudinal Video Study on Communicating Status and Intent for Self-Driving Vehicle-Pedestrian Interaction." Proceedings of the 2020 CHI Conference on Human Factors in Computing Systems, ACM, 2020, pp. 1-14. May have been otherwise available before 2020.
Xing et al. "Toward human-vehicle collaboration: Review and perspectives on human-centered collaborative automated driving." (2021). Transportation research part C: emerging technologies, 128, 103199. May have been otherwise available before 2021.
Tabone et al. "Vulnerable road users and the coming wave of automated vehicles: Expert perspectives." (2021). Transportation research interdisciplinary perspectives, 9, 100293 (https://www.sciencedirect.com/science/article/pii/S2590198220302049?via%3Dihub). May have been otherwise available before 2021.
Debease, Paul "Training versus Inference", Gartner, Feb. 14, 2019. (https://blogs.gartner.com/paul-debeasi/2019/02/14/training-versus-inference/).

* cited by examiner

REMOTE MONITORING WITH ARTIFICIAL INTELLIGENCE AND AWARENESS MACHINES

CROSS-REFERENCE TO RELATED APPLICATION

The present application claims the benefit of U.S. Provisional Patent Application No. 62/705,296 entitled "Remote Monitoring with Artificial Intelligence and Awareness Machines" filed Jun. 19, 2020, the contents of which is incorporated herein by reference in its entirety.

This application is a U.S. National Phase filing of International Application No. PCT/IB2021/055193 filed Jun. 12, 2021, which claims priority of U.S. Application No. 62/705,296 filed Jun. 19, 2020. Priority of U.S. Application No. 62/705,296 is also claimed by U.S. application Ser. No. 17/303,497 filed May 31, 2021.

TECHNICAL FIELD

The present disclosure relates generally to artificial intelligence, real-time processing, and, more particularly, a system and method for intelligent awareness as an aspect of a community wide care.

BACKGROUND

Pandemics may be inherently uncertain, undergo rapid progression, and be widely disruptive. The current COVID-19 pandemic poses pressing challenges not seen with recent pandemics. The mortality rate and contagiousness of COVID-19 is likely to be higher than that seen in the H1N1 pandemic in 2009. The 1918 Pandemic Influenza occurred in three waves across the spring, fall, and winter of 1918. The 1918 Pandemic Influenza spread globally over a year, while COVID-19 reached a global scope within weeks. Pandemic-related strain on critical care infrastructure and services (CCIS) may have made the inherent weakness of a typical in-person-care (also referred to as brick-and-mortar) model apparent. The current standard of care, financial incentive structure, and infrastructure may rely heavily on brick-and-mortar based health services. In waiting rooms, patients and non-patients may be vulnerable to exposure to COVID-19. Patients with other chronic illnesses and conditions susceptible to COVID-19 complications may be especially at risk. COVID-19 may have upended earlier best practices. The critical care system is especially strained, leaving many non-COVID-19 but traditionally high-risk patients without care. Moreover, the pandemic may have pushed care services (of type comprising at least one of health, community welfare, emergency, financial, employment, transportation, and combination thereof) at all levels to strained conditions not seen before. For example, some communities have seen their health and social care system brought to their breaking point as localities run out of personal protective equipment (PPE), ICU (intensive care unit) beds, and ventilators, among others. For some communities, rationing care services (e.g., health services) may have been unavoidable.

In an embodiment, the crisis may not be limited to healthcare. Other affected care services comprise at least one of infrastructure, service, wellbeing in general, and combination thereof and relate to areas comprising at least one of health, welfare, emergency, finance, employment, transportation, entertainment, logistics, retail, governance, and combination thereof. Communication and data voids due to uncertainty around the trajectory of COVID-19 may have caused fear and misinformation. Awareness machines and AI may have the capability and readiness to make a wider constructive impact not only within local communities, but globally.

In an embodiment, one or more care services may be affected by one or more crisis (e.g., other than COVID-19) due to one or more adversity of a basis comprising at least one of: environmental (e.g., natural disturbances, species extinction, etc.), shortages and wastages (e.g., of resources, talents, etc.), societal (e.g., social disturbance), business (e.g., processes related to supply chain, distribution, procurement, fulfillment, etc.), attacks (e.g., wars, demonstrations, cyber-attacks, attacks on goodwill and reputation, and combination thereof), and combination thereof. In an embodiment, the one or more crisis may be due to one or more change (e.g., anticipated, unanticipated, avoidable, unavoidable, etc.) of a basis comprising at least one of: infrastructure (e.g., related to autonomous driving and its support structure such as electric grid, supply and refueling, utility provisioning, etc.), transportation (e.g., road conditions, autonomous driving, public transportation, etc.), societal (e.g., way of life, civic constructs, institutions, etc.), behavioral (e.g., individual habits, crowd dynamics, sentiment, cognitive decision making and reasoning in general, etc.; other examples are behaviors related to autonomous driving, new technologies, new ideas, etc.), markets (e.g., financial, housing, wholesale and retail, etc.), and combination thereof.

SUMMARY

One or more crisis may be overcome with awareness machines and their role in one or more AI-based communitywide care comprising at least one of: domain monitoring (e.g., comprising at least one of collection, aggregation, analysis, transformation, delivery, presentation, persistence, and combination thereof of data); information exchange (e.g., comprising at least one of retrieval, processing, delivery, presentation, and communication in general); intelligence generation (e.g., for purposes comprising at least one of prioritizing, coordinating, assessing risk and opportunity, choosing, decision-making in general, and combination thereof); and combination thereof.

In an embodiment, a communitywide care for prevention and mitigation of the COVID-19 disease is designed for real-time remote monitoring of an event. The communitywide care is designed to take real-time observations of patient symptoms, process the observation to detect an onset of an instance of the event and generate one or more intelligence (e.g., of a basis comprising at least one of: the onset, the instance, the event, and combination thereof), and, upon detection, deliver a notification constructed from the intelligence.

In an embodiment, the communitywide care (supported by a first system) exchanges one or more piece of information (e.g., comprising one or more intelligence, one or more observation, etc.) with one or more second communitywide care (supported by one or more second system), to generally improve performance of detection of an onset (of the instance of the event) and improve quality of the intelligence.

In an embodiment, a performance measure for a communitywide care is formulated with a first metric (of a basis, for example, comprising at least one of confusion matrix, truth table, Bayesian network, and combination thereof) and a second metric. The evaluated first metric for a first observation of the communitywide care and the evaluated second metric for a second observation of the communitywide care are provided to one or more entity, which enables the one or more entity to gain one or more insight of a basis comprising at least one of: performance of the communitywide care, viability of the communitywide care, improvement of the performance measure, and combination thereof.

The foregoing has broadly outlined the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 1:
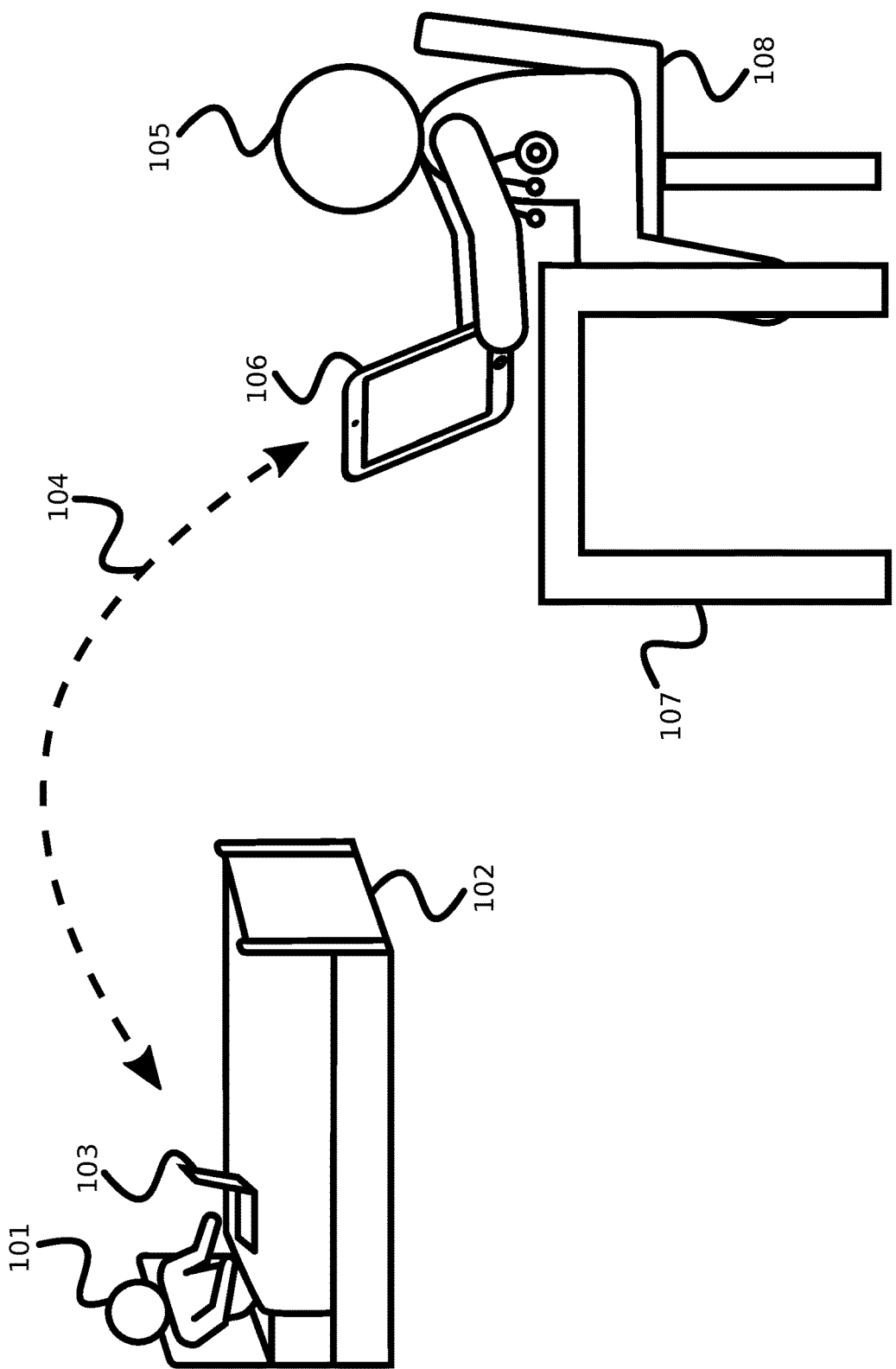
FIG. 1 illustrates a block diagram of an on-demand monitoring system for healthcare in accordance with an embodiment related to the present application.

Various features and advantageous details are explained more fully with reference to the non-limiting embodiments that are illustrated in the accompanying drawings and detailed in the following description. Descriptions of well-known starting materials, processing techniques, components, and equipment are omitted so as not to unnecessarily obscure the invention in detail. It should be understood, however, that the detailed description and the specific examples, while indicating embodiments of the invention, are exemplary by way of illustration only, and not by way of limitation. Various substitutions, modifications, additions, and/or rearrangements within the spirit and/or scope of the underlying inventive concept will become apparent to those skilled in the art from this disclosure.

As used herein, the term "communitywide care" refers generally to one or more effort toward the welfare of a community of elements comprising at least one of its members, its assets, its environment, and combination thereof, wherein: the scope of a communitywide care may be on various scales of type comprising at least one of small, medium, mass-scale, and combination thereof one or more administrator of type comprising at least one of planner, decision maker, researcher, leader, executive, and combination thereof may be responsible for the execution of the welfare efforts; and the one or more administrator may in general benefit from one or more system and one or more method. One or more communitywide care may allow one or more community to overcome one or more adversity comprising at least one of disaster, violation, disturbance, inefficiency, loss in general (for example, a lost gain comprising at least one of lost opportunity, lost benefit, lost relief, and combination thereof may also be regarded as a loss), and combination thereof. As used herein, the term "severity" refers generally to a set of one or more adversity. The term "high-severity" generally refers to adversity of high degree, comprising at least one of: need for urgent response (comprising at least one of mitigation, containment, symptom relief, triage, intervention in general, help in general, and combination thereof); need for prioritization of care; imminent threat of catastrophe; possibility of loss (of type comprising at least one of irreversible, unacceptable, and combination thereof); and combination thereof. The term "low-severity" generally refers to adversity of low degree that may require action comprising at least one of: continued observation, precautionary measures, anticipatory preparation, vigilance (e.g., to identify possible onset of, diagnose potential extent of, and avoid loss due to high-severity), and combination thereof.

In general, a performance measure of a communitywide care (and its system) for a target community may relate to the communitywide care's (and its system's) ability comprising at least one of: to serve the target community, minimize loss and maximize gain for one or more beneficiary (comprising at least one of the target community, administrator of the communitywide care, administrator in general, member of the target community, commercial and government entities related to the target community, and combination thereof), and combination thereof. One or more administrator may construct one or more metric for the performance measure to convert one or more observation of one or more operation related to the communitywide care into a concrete mathematical structure comprising at least one of definition, quantity, matrix, network, complex relationship, distribution, metadata, and combination thereof; the concrete mathematical structure generally represents a unique measure of the one or more operation with respect to the one or more metric and its corresponding communitywide care's performance measure.

In an embodiment, for a communitywide care and its supporting system, one or more performance measure may be identified and evaluated for a component comprising at least one of: a part of the communitywide care, a part of the supporting system, the communitywide care, the supporting system, and combination thereof. One or more metric may formulate the one or more performance measure. One or more first computation of the one or more metric for a first operation (e.g., an execution, a run, an instance) of the communitywide care (and the supporting system) may be identified as one or more first performance indicator for the first operation. A plurality of second computations of the one or more metric for a plurality of second operations of the communitywide care (and the supporting system) may be identified as a plurality of second performance indicators for the plurality of second operations. One or more entity (comprising at least one of administrator, system, user, beneficiary in general, and combination thereof) may receive information—comprising at least one of: the one or more performance measure, the one or more metric, the one or more first performance indicator, the plurality of second performance indicators, and combination thereof—to generally benefit (e.g., as a beneficiary, operator, or overseer in general of the communitywide care) and gain one or more insight comprising at least one of:

a. performance of the communitywide care (and the supporting system) related to one or more measure comprising at least one of effectiveness, efficacy, and combination thereof;

b. viability of the communitywide care (and the supporting system) related to one or more measure of a basis comprising at least one of economic, social, jurisdictional, scientific, business, environmental, and combination thereof.

c. the nature in general of the communitywide care (and the supporting system), related to one or more measure of a basis comprising at least one of correlation, covariance, bias in general, rule of thumb, inference framework, logic and rules, accuracy, event distribution (to evaluate, for example, likelihood of a catastrophic event, possibility of a tail-end or rare event, propensities in general, etc.) in general; and d. combination thereof.

In an embodiment, one or more administrator may configure one or more system for a communitywide care to monitor one or more severity of one or more community in order to enhance the welfare of the one or more community and its elements, wherein the one or more system is aware of the one or more community and related one or more domain, and wherein the system is driven by one or more AI. As an aspect of the monitoring, the one or more system may observe the one or more domain in real-time, collect information from one or more sources, generate intelligence that is value-adding and actionable, execute one or more action according to the one or more administrator's specification (e.g., of the one or more severity and its degree, generally based on the one or more administrator's expectation), and deliver an alert (e.g., to induce one or more action) to recipients comprising at least one of: the one or more administrator, user, system, and combination thereof. The one or more administrator may specify one or more alarm (e.g., of type comprising high-severity, patient noncompliance, and combination thereof) as one or more part of the configuration, wherein the monitoring one or more system may generate one or more intelligence comprising at least one of prediction, forecast, recommendation, action, algorithm, shortcut (e.g., a rule of thumb), notification (e.g., to the administrator), system (e.g., a first intelligent system, a second intelligent sub-system, etc.), and combination thereof.

In an embodiment, the system's performance measure comprising at least one of effectiveness, efficacy, viability (e.g., a measure of a basis comprising at least one of economic, social, jurisdictional, scientific, business, environmental, and combination thereof), efficiency, accuracy in general, and combination thereof may be derived from one or more metric (e.g. confusion matrix, truth table, Bayesian networks, etc.) by comparing one or more intelligence generated by the system with the one or more administrator's expectation of the one or more intelligence. For a sample observation of the one or more domain by the system (e.g., an observation sampled by methods—which may be predetermined—comprising at least one of: by devices, at certain time intervals, with normalization, after preprocessing, and combination thereof), the one or more intelligence generated by the system is denoted as a prediction, and the corresponding one or more administrator's expectation of the one or more intelligence is denoted as a truth-value corresponding to the prediction. In an embodiment, as convention, predictions may be partitioned into distinct classes, with every prediction class corresponding to a class of truth-value.

In an embodiment, observing one or more event monitored by a first system (for communitywide care) results in N observations with N predictions and N corresponding truth-values. In this embodiment, for clarity, and not by way of limitation, one observation is processed by the first system to generate one prediction, wherein, the prediction is compared (e.g., algebraically, cognitively, statistically, etc.) with one truth-value corresponding to the observation. The first system generates a F×F sized square first confusion matrix where F is the number of distinct (generally disjoint, for example, as predetermined by one or more administrator) prediction classes. An entry in the matrix at row i and column j is denoted by $n_{ij}$, where $1 \leq i \leq F$ and $1 \leq j \leq F$. An entry $n_{ij}$ represents the number of sample observations with a truth-value of class i that is predicted by the first system to be of class j. The number of correct predictions of the class i is given by the entry ($n_{ij}$:j=i). The counts of correctly predicted observations for the F classes exist in the main diagonal (e.g., $n_{ij}$:j=i) entries of the first confusion matrix. An accuracy (AC) of the first system's N predictions (from the N observations) may be given by $$AC = \frac{\sum_{i=1}^{F} (n_{ij})_{j=i}}{\sum_{i=1}^{F} \sum_{j=1}^{F} n_{ij}}$$

The accuracy of the first system is a type of performance indicator typically derived from a metric of a performance measure for the first system. The non-diagonal members of the first confusion matrix ($n_{ij}$:j≠i) may provide insights on biases, need for normalization of the first confusion matrix, and one or more part of the first system that may need further fine tuning. In an embodiment, a normalized second confusion matrix of a fine tuned second system may generate insightful feedback on one or more aspect (comprising at least one of design, learning, communication, feedback, and combination thereof) of the second system. The first confusion matrix and the second confusion matrix—due to their information richness—may contain information needed by heterogeneous administrators of the systems (the first system and the second system), wherein the administrators may be of type comprising at least one of professionals, community leaders, resource managers, quants (e.g., the ones fine tuning AI and cognitive intelligence generation, and generating analytical insights), systems architects, infrastructure engineers, researchers, systems, and combination thereof.

In an embodiment, for observations of an event by a system (for communitywide care), predictions comprise at least one of data set, matrix, probabilities (e.g., probability distributions), time series, and combination thereof, such that the format and presentation of the predictions match the format and presentation of their corresponding truth-values. The corresponding truth-values may be analytically compared (e.g., algebraically, cognitively, statistically, etc.) with the predictions to assess their validity. A confusion matrix for the observations for the event is derived using the results of the corresponding analytical comparisons (e.g., algebraic, cognitive, statistical, etc.). The confusion matrix is, in general, a type of metric that is formulated from a performance measure of the system in monitoring the event.

In an embodiment, a confusion matrix for a complex system (for communitywide care) may be a multidimensional matrix, wherein the dimensionality of the multidimensional matrix is a reflection of characteristics comprising at least one of: complexity of the system, possible existence of hidden variables (e.g., confounders, confounding variables, etc.), one or more need for increased granularity (e.g., higher resolution) of observation, and combination thereof. In an embodiment, the information and intelligence in a confusion matrix may be represented by one or more mathematical model of type comprising at least one of: graphical (comprising at least one of Markov networks, Markov chains, Bayesian networks, and combination thereof), probabilistic inference, time series, neural network, singular value decomposition, complex analysis (using, for example, complex analytic functions, complex numbers to represent phase shifts, etc.), and combination thereof. In an embodiment, a complex system in general (for communitywide care) may be analyzed with one or more technique comprising at least one of: matrix manipulation, matrix singular value decomposition, visual representation (e.g., for cognitive and perceptive observation and knowledge generation), intelligence extraction (using, for example, neural networks and other AI techniques), graph and network optimization, probabilistic inference, complex analysis (using, for example, complex analytic functions, complex numbers to represent phase shifts, etc.), and combination thereof.

In an embodiment, observing one or more event monitored by a first system (for communitywide care) results in N observations with N×T predictions and N×T corresponding truth-values. In this embodiment, for clarity, and not by way of limitation, one observation is processed by the first system to generate one prediction set of T predictions. For a first observation at time θ, the first system generates a first prediction set of size T: predictions for T−1 time instances in the future (for example, {θ+1 hour, θ+24 hours, θ+12 days, θ+30 days, θ+six months}) along with one prediction for time θ. A first prediction (for a first time-instance) from the first prediction set is compared with one truth-value corresponding to the first observation (and the first time-instance). The first prediction set is compared (e.g., algebraically, cognitively, statistically, etc.) with a first truth set of size T: truth-values for T−1 time instances in the future (for example, {θ+1 hour, θ+24 hours, θ+12 days, θ+30 days, θ+six months}) along with one truth-value for time θ. The first system generates a F×F×T sized first confusion matrix where F is the number of distinct (generally disjoint, for example, as predetermined by one or more administrator) prediction classes, wherein for a first time instance t (from one of the T−1 time instances in the future and one time instance for time θ) a F×F sized first square matrix represents the part of the confusion matrix for the first time instance (t).

In an embodiment, the first system monitoring the first observation at time θ generates the F×F sized first square matrix for the first time instance t, wherein a first accuracy $AC_t$ represents an accuracy derived from the first square matrix. An entry in the confusion matrix at row i, column j, and time instance k is denoted by $n_{ijk}$, where 1≤i≤F, 1≤j≤F and 1≤k≤T. An entry $n_{ijk}$ represents the number of sample observations with a truth-value of class i that is predicted by the first system to be of class j for time instance k. For the first time instance t, the number of correct predictions of the class i is given by the entry ($n_{ijk}$:j=i, k=t). The counts of correct predictions for the first time instance t for the F classes exist in the main diagonal (e.g., $n_{ijk}$:j=i, k=t) entries of the first square matrix. The first accuracy ($AC_t$) of the first system's N predictions (from the N observations) for the first time instance t is given by $$AC_t = \frac{\sum_{i=1}^{F}(n_{ijk})_{j=i,k=t}}{\sum_{i=1}^{F}\sum_{j=1}^{F}(n_{ijk})_{k=t}}$$

The non-diagonal members for the first time instance k=t of the first square matrix ($n_{ijk}$:j≠i, k=t) may provide insights on one or more need comprising at least one of: accounting for biases, normalization (e.g., of the first square matrix and the first confusion matrix), tuning of one or more part of the first system, and combination thereof. In an embodiment, the first system's, the first observation's, and the first confusion matrix's analyses comprising at least one of: normalization, fine tuning in general, and combination thereof may generate insightful feedback on one or more aspect (comprising at least one of design, learning, communication, feedback, and combination thereof) of the first system. The analyses may contain information needed by heterogeneous administrators of the systems, wherein the administrators may be of type comprising at least one of professionals, community leaders, resource managers, quants (e.g., the ones fine tuning AI and cognitive intelligence generation and generating analytical insights), systems architects, infrastructure engineers, researchers, systems, and combination thereof. The first accuracy of the first system is a type of performance indicator typically derived from a metric of a performance measure for the first system.

In an embodiment, a community may be described by one or more characteristic of a basis comprising at least one of: geographical; jurisdictional; social; based on one or more shared characteristic comprising at least one of belief, principle, convention, physical property, and combination thereof; regional; and combination thereof. Two or more communities may share one or more of their characteristic type.

In an embodiment, a communitywide care comprises at least one of: domain monitoring (comprising at least one of collection, aggregation, analysis, transformation, delivery, presentation, persistence, and combination thereof of data); information exchange (comprising at least one of retrieval, processing, delivery, communication in general, and combination thereof); intelligence generation (for purpose comprising at least one of predicting, prioritizing, coordinating, assessing risk and opportunity, choosing, decision making in general, and combination thereof); advancing knowledge and skill in general; execution in general (e.g., execution of decisions); and combination thereof.

In an embodiment, for a community, a communitywide care may be related to a service of type comprising health, welfare, emergency response, finance, employment, transportation, entertainment, logistics, retail, governance, education, communication, information dissemination in general, and combination thereof. As a part of the service, a system (for communitywide care) observing a domain may process events in real-time and generate information of type comprising at least one of: analytics, intelligence (e.g., from cognitive intelligence and from AI in general), notification, metadata, extract and synopsis, narrative (e.g., in a predetermined format for the benefit of an end user), and combination thereof. The performance (comprising at least one of effectiveness, efficacy, and combination thereof) and viability (a measure of a basis comprising at least one of economic, social, jurisdictional, scientific, business, environmental, and combination thereof) of the service, the system, the communitywide care in general, the community, one or more end user response, and combination thereof, among others, may be evaluated by computing one or more metric (of a basis comprising, for example, confusion matrix, truth table, Bayesian network, etc.), wherein the computed one or more metric may be referred to as one or more performance indicator. Insights and feedback due to the one or more metric are used to tune the service, the system, the communitywide care, the community, the one or more end user response, and combination thereof. The term "tune" refers to performance improvement in general within constraints of parameters comprising at least one of: resource, knowledge, information, processing time, cultural norms, jurisdiction, sentiment, and combination thereof.

In relation to a communitywide care of a community, for a system monitoring a domain, real-time monitoring differs from and offers benefits over on-demand monitoring. As used herein, real-time processing (e.g., observing, monitoring, etc.) of an event in progress, on one hand, may indicate an inconsequentially small time-lag between a snapshot of the event and processing of the snapshot (e.g., observing the snapshot), while on the other hand, the processing (e.g., observing) may be continuous over the entire duration of the event.

In an embodiment for a system (for communitywide care) monitoring an event, in relation to the system's one or more aspect (comprising at least one of design, development, implementation, operationalization, performance verification and tuning, testing, training, and combination thereof), real-time observations of the event are characterized by:
  a. One or more small first time-lag between consecutive pairs of snapshots of the event (e.g., to maximize resolution of the observations);
  b. One or more small second time-lag between a snapshot of the event and processing of the snapshot by the system;
  c. The first time-lag and the second time-lag being on the same order of magnitude; and
  d. Continuity of the real-time observations being maintained over the entire duration of the event;
wherein a snapshot may represent an observation and its aspect comprising at least one of: data-point, data-point harvesting, and combination thereof. In general, the term "data-point" refers to a set of relevant facts (e.g., vitals for COVID-19 patients) along with concurrently collected date-and-timestamp from observing an event (e.g., COVID-19 progression) in a domain.

In an embodiment, for a first system monitoring a first event in a first domain, a first process is episodic and on-demand in nature, wherein one or more episode of the first process is generally initiated by an actor comprising at least one of administrator, user, system, and combination thereof. The monitoring by the first system may be valid over time intervals of the one or more episode, wherein the time intervals represent one or more fraction of the first event's duration, and the one or more on-demand first process is generally regarded as time dependent. In an embodiment, for a second system monitoring the first event in real-time, one or more second process of the second system is continuous over the duration of the first event, wherein the one or more second process is generally regarded as time independent.

In an embodiment, traditionally, engineers—generally during design of an on-demand monitoring system—may accept a tradeoff between data resolution and sampling continuity. By design, on-demand monitoring, to allow for human consumption of data, makes a compromise comprising at least one of: loss of sampling continuity, loss of resolution, and combination thereof. In an embodiment, for a communitywide care for prevention and mitigation of the COVID-19 disease, 12 days are regarded as the progression duration of the disease. For a first operation of real-time monitoring, a first real-time observation (e.g., with biosensors) of symptoms for a patient involves taking observations every second for the 12-day duration. The first real-time observation and the first operation are independent of time of day during the 12-day duration, and the first operation and the first real-time observation are generally regarded as time independent. In an embodiment, for a second operation of on-demand monitoring, a ten-minute episodic second observation of sensors once on each of the 12 days, whether at home, online, or in a clinical setting, is not real-time. The second operation and the second observation are not real-time. During the second operation, a second presentation of COVID-19 symptoms associated with high-severity—if it occurs between two consecutive ten-minute second observations—would go unobserved by the second operation; thus, the second presentation may go unnoticed by the patient, doctors, and other caregivers. In an embodiment, for a third operation of on-demand monitoring, sporadic five-minute third observations are carried out throughout the day during the 12 days, whether at home, online, or in a clinical setting. During the third operation, a third presentation of COVID-19 symptoms associated with high-severity between two consecutive instances of the third observations would go unobserved by the third operation, wherein the third presentation may go unnoticed by the patient, doctors, and other caregivers. The third observations and the third operation are not real-time. In an embodiment, a healthcare provider comprising at least one of nurse, health technician, health researcher, and combination thereof may represent a doctor; one or more doctor may also oversee a system of communitywide care as an administrator.

In an embodiment, a communitywide care for prevention and mitigation of the COVID-19 disease is designed for real-time monitoring, wherein the disease progression is estimated to take 12 days to complete. The communitywide care is designed to take one observation (e.g., data-point) of the patient symptoms (e.g., with biosensors) per second. A first operation of the communitywide care (e.g., monitoring of a first COVID-19 patient) may deviate from the design guidelines of the communitywide care and introduce a defect comprising at least one of: patient noncompliance (e.g., patient knowingly removing a sensor, unknowingly removing a sensor, etc.), downtime, connectivity and resource (comprising at least one of power, network, broadband, compute, and combination thereof) interruption, equipment malfunction, and combination thereof. A second operation of the communitywide care may suffer from challenges and may otherwise introduce defects, comprising at least one of implementation and execution errors (e.g., of administrators), shortcomings of human communication and compliance (related to, for example, training and instructions), introduction of human biases, and combination thereof. In an embodiment, the defects (from the first operation and the second operation) may be overcome by compensating actions of actors comprising at least one of: the administrators, experts, awareness machines and AI (e.g., by training and online learning), systems, and combination thereof.

In an embodiment, for one or more communitywide care supported by one or more system, one or more awareness of the system (e.g., an AI based system) is characterized by nuances of a basis comprising at least one of: diversity of information, diversity of source of information, redundancy of information, redundancy of source of information, frequency of information, recurrence (or lack thereof) of information, diversity of intelligence, redundancy of intelligence, shades of intelligence (e.g., potentially contradictory knowledge, maintaining and improving both sides—optionality in general—of a decision, working within a gray area of knowledge, etc.), and combination thereof. In an embodiment, the nuances represent higher-order knowledge (e.g., knowledge of knowledge, metadata in general, knowledge as a tool to generate new knowledge, learning to learn, etc.) as an aspect of the one or more awareness. In an embodiment, one or more cognitive intelligence of the system comprises at least one of: intelligence, awareness (e.g., of one or more domain, self-awareness, awareness of purpose in general, etc.), autonomy (e.g., setting, planning, and attaining goals), adaptability in general, and combination thereof. In an embodiment, cognitive intelligence may be in general characterized by awareness with a basis comprising at least one of: intelligence and its awareness, autonomy and its awareness, adaptability and its awareness, domain awareness, multi-domain awareness, global awareness, awareness and its awareness, and combination thereof.

FIG. 1 illustrates system 100 in accordance with an embodiment of the present application. FIG. 1 illustrates on-demand remote monitoring of patient 101 at his home in bed 102 with laptop 103 (as an audio-video equipped portable device) by doctor 105 at an office (with desk 107 and chair 108) using tablet 106 (as an audio-video equipped mobile device). At a mutually coordinated time, patient 101 and doctor 105 initiate communication 104 (as audio-video communication). Communication 104 may be subject to one or more restriction (comprising at least one of: cognitive limitations, communication limitations, scalability limitations, lack of proactive involvement, and combination thereof) of patient 101 and doctor 105. The scalability limitations may relate to a shortcoming comprising at least one of: a first inability of a first doctor to simultaneously on-demand monitor more than a handful of remote patients, a second inability of a second doctor to effectively on-demand monitor more than one patient at a time, a third inability of more than a handful of third doctors to concurrently communicate with an on-demand monitored patient, and combination thereof.

In an embodiment, COVID-19 is a fast progressing disease fraught with uncertainties, wherein sudden onset of life-threatening conditions in previously symptom-free patients is reported. Monitoring of the disease may benefit from emulating data collection frequencies and continuity used in an ER (emergency room) environment and from collecting and processing readings for the disease in real-time (e.g., continuously for almost every second over the duration of disease progression). In an embodiment, an instance of real-time data collection and processing for COVID-19 may involve recording each relevant vital on the order of a second for about two weeks or until the infection is cleared.

In an embodiment, a COVID-19 patient is monitored in real-time remotely (e.g., at the patient's home) by a system (for communitywide care) for an onset of high-severity. The system is aware of one or more domain related to the patient, doctors, paramedics, hospitals, and related community in general, and a data-point is harvested about every second wherein the data-point represents a snapshot of the patient's condition that may allow the patient's doctor to arrive at a diagnosis with reasonable confidence. Upon onset of a first high-severity, the patient's doctor, hospitals, paramedics, and other relevant administrators of the system are notified. The doctor reviews intelligence and metadata associated with the first high-severity, and the paramedics, in coordination with the doctor, transport the patient to a hospital. Benefits of the system may comprise at least one of: the patient beginning treatment for the high-severity within the shortest possible time; avoidance of spread of the disease that might have been caused by the patient visits to the doctor's office, waiting in the hospital waiting room, and related transportation; optimal usage of hospital resources and CCIS; increased community moral due to availability of remote communitywide monitoring (as part of one or more communitywide care) for COVID-19 low-severity in homes and availability of traditional support structures (e.g., the patient's family); reduced exposure of high-risk patients (e.g., patients with preexisting COVID-19 morbidity markers) to COVID-19; and combination thereof. The monitoring of the more than a handful of remote patients is referred to by the term "communitywide monitoring".

Figure 2:
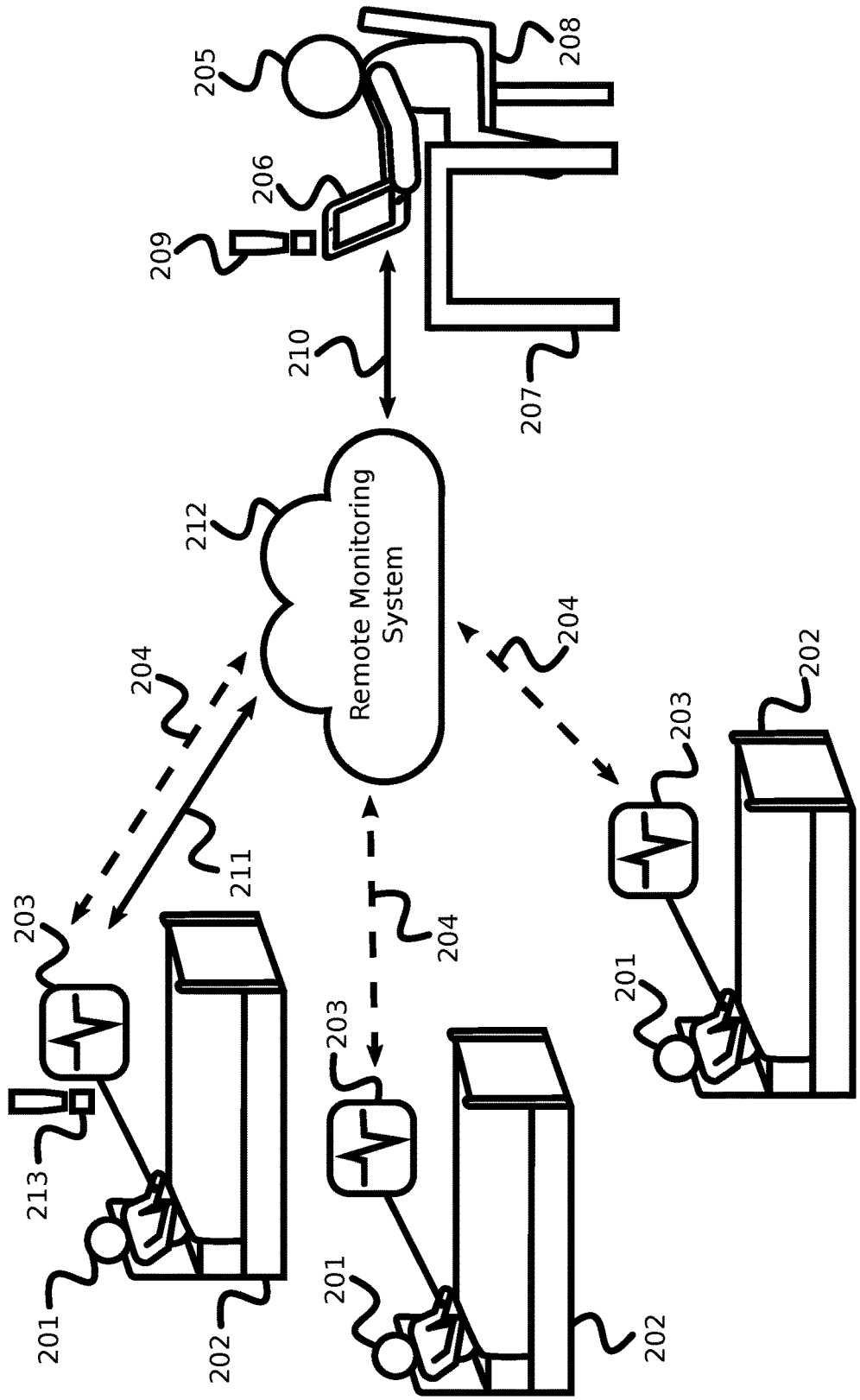
FIG. 2 illustrates a block diagram of a real-time monitoring system for a communitywide care related to healthcare in accordance with an embodiment of the present application.

FIG. 2 illustrates system 200 in accordance with an embodiment of the present application. FIG. 2 illustrates a first communitywide care for mitigating COVID-19 in a target community wherein more than a handful of patients (though, for clarity, three are shown)—patients 201 at their homes in their beds 202—are monitored by doctor 205 at an office (with tablet 206, desk 207, and chair 208). Key 214 indicates descriptions of vitals—blood oxygen saturation level in percentage, body temperature in degrees Fahrenheit, heart rate in beats per minute, and breathing rate in breaths per minute—that, along with timestamp, comprise a data-point. Each of the patients 201 is monitored in real-time with a vitals observation device on his left arm. In real-time, a data-point (represented by data-points 203) is generated by the vitals observation device and sent to system 212 through communication 204 for further processing comprising at least one of: real-time analytics, intelligence generation, learning, identification of high-severity, notification to administrator, narrating and formatting (e.g., to benefit end users, devices, and systems), and combination thereof. Doctor 205, as an administrator, configures system 212 with a customization comprising at least one of: conditions and rules for high-severity, criteria for system performance and validation (e.g. a confusion matrix), process automation, and combination thereof, wherein doctor 205 may not need to interact with each individual patient in the group of patients 201. For the first communitywide care, by design: when a patient (from patients 201) exhibits onset of high-severity, system 212—in real-time—receives corresponding data-points through communication 204, identifies the high-severity and its onset, generates a first notification (of a basis, for example, comprising at least one of intelligence, metadata, narrative, and combination thereof) intended for doctor 205, delivers the first notification to doctor 205, and executes one or more automation configured by doctor 205. Upon delivery of the first notification to doctor 205, system 212 waits for input from doctor 205, while concurrently executing one or more automation configured in the system.

FIG. 2 further illustrates an onset of high-severity 213 due to low blood oxygen saturation level and high breathing rate for a first patient from the group of patients 201. The first patient is not aware of high-severity 213 and the onset of high-severity 213. System 212—in real-time—receives one or more data-point corresponding to high-severity 213, identifies and gains awareness of the first patient and high-severity 213, generates and delivers notification 209 for doctor 205 though communication 210, and awaits response and further instructions from doctor 205. Doctor 205 acknowledges notification 209 and requests metadata of high-severity 213 by using dedicated communication 210 with system 212. Thereafter, system 212 responds to doctor 205 with requested information about the first patient and high-severity 213: system 212 initiates dedicated communication 211 to the first patient, his devices, and his home (e.g., telephone call, notifying the first patient's caregiver at home, etc.) to generate the requested information and deliver it to doctor 205. Thereafter, doctor 205 verifies and confirms high-severity 213, and notifies system 212 through communication 210 that the first patient should be admitted to a hospital for ER care. System 212 gains awareness needed for admitting the first patient to the hospital and notifies the hospital, paramedics (for transportation), and administrators (e.g., ER doctors, city officials, etc.); within minutes of the onset of high-severity 213, the first patient is admitted to the hospital ER.

For the first communitywide care in the target community, system 212 and doctor 205 may use communication 210 and 211 for one or more purpose comprising at least one of: collecting data-points from the first patient, audio-video-text conversation with the first patient or his caregiver, and combination thereof. FIG. 2 further illustrates methods that enable system 212 to gain awareness of high-severity 213, the first communitywide care, and one or more domain related to the first communitywide care in general. System 212 builds a confusion matrix to quantify and evaluate the performance and efficacy of the first communitywide care. Feedback from the confusion matrix allows system 212 to tune its processes, intelligence, communication, and the first communitywide care in general.

In an embodiment, FIG. 2 illustrates, for a first communitywide care for mitigating COVID-19 in a target community, advantages of real-time monitoring over episodic on-demand monitoring. Once configured (e.g., with a first configuration) by doctor 205 and first administrators, system 212 is the sole entity responsible for real-time monitoring of patients 201. Unlike for on-demand monitoring, workload and monitoring responsibility of doctor 205 and the first administrators does not increase proportionally with an increase in the number of monitored patients 201. Due to its fine granularity and its large volume, real-time data (through communication 204) in its raw format from patients 201 would inundate doctor 205, the first administrators, and first users in general. To mitigate the inundation, system 212 may autonomously monitor first low-severities of patients 201, requiring a minimal intervention (e.g., interaction with patients 201) from the doctor 205, the first administrators, and the first users; the minimal intervention may comprise at least one of: essentially no interaction (e.g., with patients 201, system 212, etc.), initial patient consultation (e.g., to prescribe remote monitoring) and training, checking up on patients 201 subject to availability of doctor 205, answering patient questions, and combination thereof. Only upon the onset of high-severity 213 for a first patient: system 212 detects high-severity 213 and notifies doctor 205 through communication 210 in a format required by doctor 205; the first administrators and the first users are not notified of the onset (e.g., per the first configuration); system 212 receives from doctor 205 an acknowledgement of receipt of the notification; system 212 waits for further instructions from doctor 205; doctor 205 initiates dedicated communication 211 with the first patient through communication 210; doctor 205 takes over—from system 212—the primary responsibility of care (of type comprising at least one of monitoring, diagnosis, referrals, and combination thereof) for the first patient; and thereafter, system 212 supports doctor 205 in caring for the first patient. Thus, system 212 delivers one or more high-severity notification when needed (e.g., at onset of high-severity 213), only to the intended one or more recipient (e.g., doctor 205), and in the format (e.g., narrative, metadata, intelligence, etc. suitable for doctor 205) needed by the one or more recipient. The format of the one or more high-severity notification for doctor 205 comprises at least one of: metadata of high-severity 213, intelligence related to high-severity 213, COVID-19 comorbidities (e.g., diabetes, hypertension, COPD or other respiratory disease, underlying vascular disease, etc.) for the first patient, relevant patient history, and combination thereof. As opposed to on-demand care, system 212 facilitates communitywide monitoring and the first communitywide care with benefits comprising at least one of scalability ease, generated cognitive AI, cognitive assistance offered to administrators (e.g., doctor 205) and other users, real-time nature of processing (e.g., in communication, AI generation, etc.), passive nature of monitoring, and combination thereof. The scalability ease—along with the other benefits—imparts to system 212 one or more ability comprising at least one of: a first ability of system 212 to simultaneously and in real-time monitor more than a handful of remote patients; a second ability of system 212 to prioritize and engage one or more second doctor if one or more second high-severity of one or more second patient presents itself at about the same time as high-severity 213 (while the first patient is monitored by doctor 205); a third ability of more than a handful of third doctors to concurrently communicate with system 212 to monitor at least one of the first patient, the one or more second patient, and combination thereof a fourth ability to carry out communitywide monitoring and the health-related first communitywide care for COVID-19; a fifth ability of system 212 to communicate, share, and coordinate with one or more fifth system to enhance and improve one or more fifth communitywide care along with the first communitywide care orchestrated by system 212; and combination thereof. In an embodiment, the fifth ability of system 212 enables it to facilitate one or more multifaceted communitywide care, wherein besides the first communitywide care—healthcare for COVID-19—system 212 orchestrates and provisions one or more second communitywide care for a purpose comprising at least one of: managing or treating chronic diseases, providing or enhancing elderly and disabled care, community (e.g., city) planning, economic and business impact, education and social services impact, regulatory and jurisdictional impact, impact on governance in general, and In FIG. 2, for a first communitywide care for mitigating COVID-19 in a target community, observation of vitals is a part of a data-point, which is described by Key 214; Key 214 includes blood oxygen saturation level in percentage, body temperature in degrees Fahrenheit, heart rate in beats per minute, and breathing rate in breaths per minute. In general, vitals significant for COVID-19 high-severity may be:

a. Blood oxygen saturation level ($SpO_2$ measured in percentage): This measures the percentage of oxygen saturation in the blood. Normal range is 95 to 100. A reading below 92 may contribute to high-severity.
b. Body temperature (fever measured in degrees Fahrenheit): Fever generally is a sign of infection. As of May 2020, a correlation between fever and COVID-19 high-severity is uncertain and under investigation. As knowledge of the correlation evolves, it may be configured into system 212 and validated using performance measures and their metrics comprising at least one of: confusion matrix formulated with feedback from one or more doctor, learning of AI in system 212, and combination thereof.
c. Heart rate in beats per minute: A heart rate above 100 beats per minute may generally be a sign of worsening COVID-19 severity.
d. Breathing rate measured in breaths per minute: Heightened breathing (e.g., breathing rate over 20) may indicate high-severity associated with COVID-19. An increase in breathing rate over a short period of time, which is associated with shortness of breath, is a prominent indicator of high-severity. A patient history of chronic respiratory diseases heightens COVID-19 severity, while above average cardiovascular fitness lessens it.

In FIG. 2, for the first communitywide care for mitigating COVID-19 in the target community, doctor 205 configures (as a precursor to system 212 generating one or more intelligence) COVID-19 severity degrees:
a. Low-severity: Doctor 205 selects a pool of patients—patients 201—from COVID-19 infected individuals in the target community for home-based communitywide monitoring based on their symptoms (e.g., fever, fatigue, myalgia, cough, sore throat, runny nose, sneezing, nausea, vomiting, abdominal pain, and diarrhea). Doctor 205 also includes in the pool high-risk (due to mortality markers comprising at least one of high blood pressure, diabetes, blood coagulation abnormalities, chronic obstructive pulmonary disease, and combination thereof) patients who show no signs of, but are suspected of having, COVID-19 infection.
b. High-severity: Doctor 205 configures in system 212 high-severity symptoms comprising $SpO_2$<92%, breathing rate greater than 25 breaths per minute, and heart rate over 100 beats per minute, wherein the symptoms are adjusted according to patients' health histories and comorbidities. Doctor 205 excludes body temperature from high-severity symptoms. Doctor 205 includes, if available, D-dimer values from a patient's blood test wherein a three-fold increase in D-dimer values may contribute to high-severity. The D-dimer values are both passively accepted and proactively accessed by system 212 from blood test laboratories.

In FIG. 2, in relation to the first communitywide care for mitigating COVID-19 in the target community, for a second patient from patients 201, the AI of system 212 reconciles first observations of $SpO_2$<92% with second observations of other vital types (e.g., breathing rate and heart rate) along with health histories of patients 201 to determine severity degree for the first observations, the second observations, and the reconciliation. System 212 determines a sixth high-severity and gains one or more awareness of the related parts of the observations (the first observations and the second observations), the reconciliation, the second patient, the health history of the second patient, and one or more responsible doctor. Thereafter, system 212 sends one or more notification of the sixth high-severity to the one or more responsible doctor, who subsequently requests additional information about the sixth high-severity. Thereafter, the AI of system 212, based on the one or more awareness, generates information comprising at least one of intelligence, metadata, narrative, and combination thereof related to the sixth high-severity and delivers it to the one or more responsible doctor in response to the request for additional information.

In an embodiment, two or more systems communicate, share, coordinate, synergize in general, and orchestrate two or more communitywide cares provisioned generally by the two or more systems, wherein the functionality, effectiveness, viability, and efficacy of the two or more communitywide cares may improve. A third communitywide care may originate from the two or more communitywide cares, wherein the third communitywide care may improve (over the two or more communitywide cares) in general due to the two or more systems' aspect comprising at least one of communication, sharing, coordination, orchestration, synergy in general, and combination thereof; the third communitywide care is generally referred to by the term "multifaceted communitywide care".

In an embodiment, for a community, a first system for a first communitywide care for healthcare, a second system for a second communitywide care related to transportation (e.g., public and private transportation), and a third system for a third communitywide care related to planning (e.g., business, school, and public service closures) perform their respective communitywide monitoring, carry out real-time processing, and provision services in isolation from one another. A first interface facilitates among the three systems (the first system, the second system and the third system): communication, sharing, coordination, and orchestration. Upon activation of the first interface, the respective communitywide cares of the three systems may provide additional functionality, optimize performance, and increase efficacy for one or more of the three systems. As an example, the first system related to healthcare may benefit from information (e.g., notifications, metadata, intelligence, and narrative in general) related to transportation and planning (e.g., to estimate transportation time for a critical patient from a home or a business to a hospital); the second system related to transportation may benefit from information related to healthcare and planning (e.g., to estimate—as an infectious disease spreads in the community—passenger load factors for public transportation); and the third system related to planning may benefit from information related to healthcare and transportation (e.g., for planning and execution—as an infectious disease spreads in the community—related to closures, social distancing, and quarantine facilities). Upon the activation of the first interface, one or more of the three systems may provision new or added functionality, improve effectiveness, expand viability (e.g., a measure of a basis comprising at least one of economic, social, jurisdictional, scientific, business, environmental, and combination thereof), and increase efficacy for the benefit of the community, wherein the respective communitywide cares for the one or more three systems may upgrade to their respective multifaceted communitywide cares.

Figure 3:
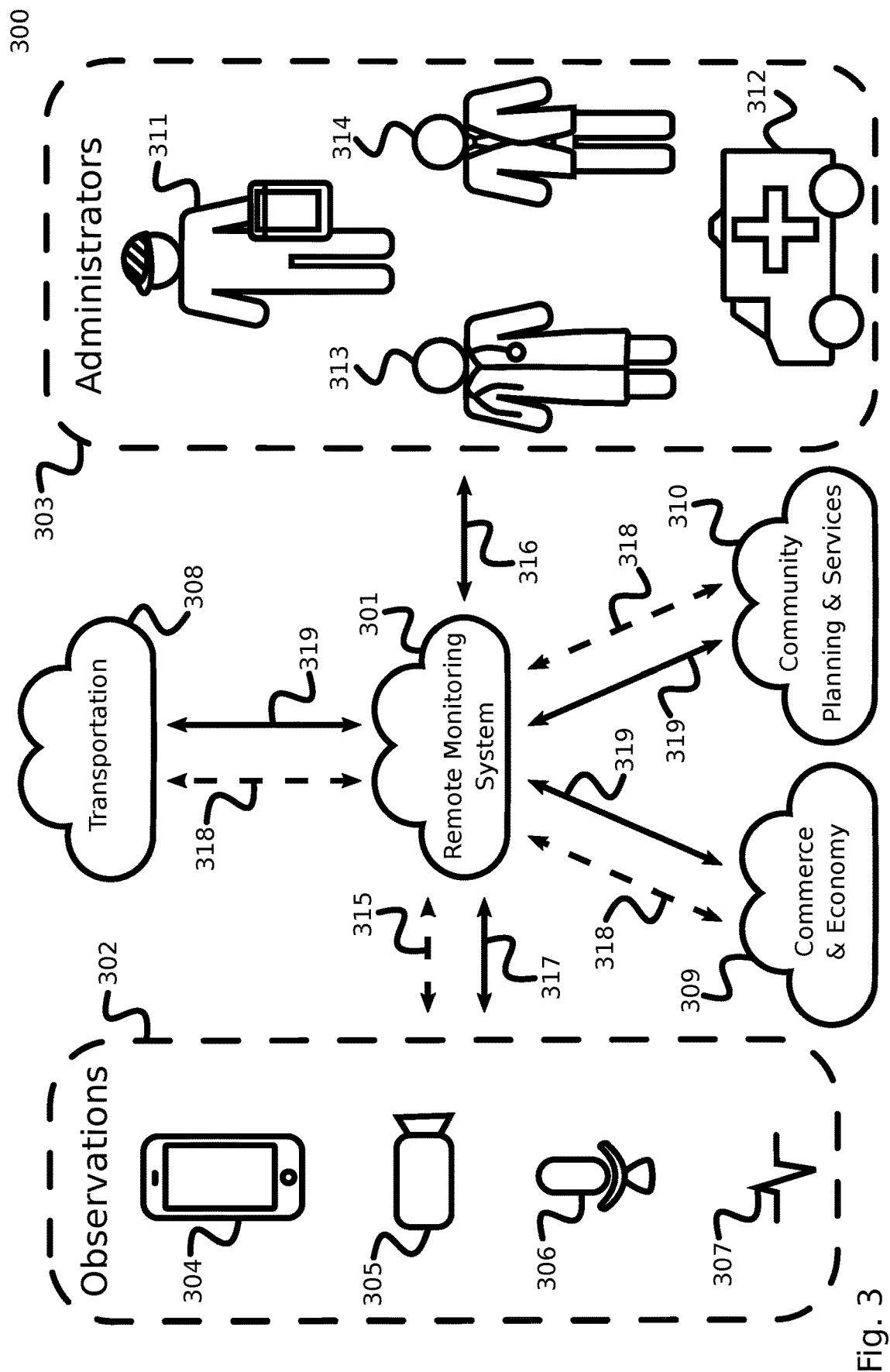
FIG. 3 illustrates a block diagram of a multifaceted communitywide care system in accordance with an embodiment of the present application.

FIG. 3 illustrates system 300 in accordance with an embodiment of the present application. In FIG. 3, system 301 supports a first communitywide care—related to healthcare—for containment and mitigation of COVID-19 spread by remotely monitoring (e.g., monitoring patients at home) first patients with low-severity in one or more first community. System 301 has a first ability to make real-time (through communication 315) observations 302 from the first patients' device 304 (mobile or otherwise), video 305, audio 306, and vitals 307 (readings comprising at least one of: blood oxygen saturation level in percentage, body temperature in degrees Fahrenheit, heart rate in beats per minute, breathing rate in breaths per minute, and combination thereof) to detect onset of a second high-severity for a second patient (who is an individual member from the group of the first patients being monitored) and notify (through communication 316) doctors 313—and, if necessary, provide additional information (comprising at least one of metadata, intelligence, narrative in general, and combination thereof) to doctors 313 (through communications 316 and 317). In isolation, system 301 is limited to the first ability. System 301 may further interface (to facilitate a capability comprising at least one of communication, sharing, coordination, orchestration, and combination thereof) with: system 308, which supports a second communitywide care related to transportation (e.g., public and private transportation) and paramedics 312; system 309, which supports a third communitywide care related to commerce and economy (e.g., economics, employment, etc.) overseen by executives 314; and system 310, which supports a fourth communitywide care related to community (e.g., city) planning and services managed by community planners 311. The interfacing enhances the first ability of system 301 and transforms it into a multifaceted second ability. System 301 interacts with systems 308 and 310 (through related real-time communications 318 and episodic communications 319) to gain and incorporate intelligence related to system 308 (transportation), paramedics 312, system 310 (community planning and services), and community planners 311 to identify a second hospital as an optimal choice for the second patient and to minimize the transportation time of the second patient to the second hospital. System 301 (through communication 316) recommends that doctors 313 contain the second high-severity by transporting the second patient to an ER of the second hospital. Doctors 313 evaluate the recommendation and the associated metadata (e.g. the reasoning behind the recommendation) and accept the recommendation. The system 301 notifies paramedics 312, who transport the second patient to the second hospital.

In FIG. 3, various administrators (303)—313, 312, 314, and 311—supervise the various systems-301, 308, 309, and 310, respectively. In an embodiment, an AI system (e.g., an autonomous AI entity, an aware system, a system with global awareness, etc.) may—as an administrator—oversee one or more first system related to one or more communitywide care. In an embodiment, an AI system may collaborate with administrators 303 to supervise the various systems (301, 308, 309, and 310), wherein the collaboration comprises at least one of sharing, substitution, coordination, acting as autopilot, acting as standby, synergizing in general, and combination thereof.

In FIG. 3, communications (315, 316, 317, 318, and 319; and in FIGS. 2: 204, 210, and 211) may be of type comprising at least one of: system-to-system, system-to-user-device (e.g., in FIG. 2, system 212 communicates with tablet 206 of doctor 205 and sensors associated with data-point 203; and in FIG. 3, system 301 communicates with devices for observations 302: 304, a patient's mobile device; 305, a patient's video camera; 306, a patient's microphone; and 307, a patient's biosensor for observing the patient's vitals), system-to-user-interface (e.g., voice input, keyboard input, biometric input, etc.), and combination thereof. The communications may facilitate one or more information exchange over one or more infrastructure comprising at least one of: networks (of type comprising at least one of local area, wide area, wireless, and combination thereof), the cloud (e.g., network cloud), airwaves (comprising at least one of: Bluetooth, ultra-wideband, spectra in general, and combination thereof), Internet, and combination thereof.

In FIG. 3, system 301 supports the first communitywide care related to healthcare and is administered by doctors 313; system 308 supports the second communitywide care related to transportation and is administered by first responders—shown as paramedics 312; system 309 supports the third communitywide care related to commerce and economy and is administered by executives 314; and system 310 supports the fourth communitywide care related to community planning and services and is administered by community planners 311. The four systems that support the four communitywide cares interface through real-time communication 318 and episodic communication 319. The interfaces transform the four communitywide cares into their respective multifaceted communitywide cares. As a first example, a multifaceted fifth communitywide care improves utilization planning (by interacting with system 301 and system 308 as it relates to first-responder transportation) to improve estimations of current and future hospitalizations related to COVID-19 high-severity; the multifaceted fifth communitywide care also monitors supply chain related to PPE (personal protective equipment) by interacting with system 309. As a second example, a multifaceted sixth communitywide care (e.g., due to interaction of system 309 with system 301, system 308, and system 310) that monitors and predicts commerce and economic activity benefits from information on real-time COVID-19 statistics (e.g., low-severity, high-severity, and asymptomatic population) and herd immunity status of the one or more first community in assessing COVID-19 impact.

In an embodiment, one or more administrator of a system for a communitywide care may use one or more performance measure for purposes comprising at least one of: improving performance; facilitating decision making; evaluating one or more of effectiveness, efficiency, viability, and efficacy of the system and the communitywide care; and combination thereof. The one or more administrator may utilize one or more metric to formulate the one or more performance measure. The one or more metric may be constructed using techniques comprising at least one of: quantifying, giving structure (e.g., generating matrices, networks, complex organizations, etc.), generating classes (e.g., bins), analyzing in general (e.g., statistical testing, clustering, etc.), constructing by convention (differentiating, for example, between urban and rural, literate and illiterate, GAAP and non-GAAP for reporting, etc.), and combination thereof. The one or more administrator may gain, with respect to the one or more performance measure, abilities comprising at least one of: comparing systems in general (between, for example, two systems, two operations of a system, two runs of system, two configurations of a system, etc.), keeping records (related to, for example, the operation and use of the communitywide care), grading (e.g., ranking) a plurality of systems (with respect to, for example, fitness for service, profitability, environmental friendliness, efficacy, efficiency, etc.), optimally designing a system (using, for example, controlled testing, simulation, analytics of historic performance measures, etc.), generating higher-order knowledge of a system (e.g., metadata, simplification etc.), generating AI to administer one or more part of the system, and combination thereof.

In FIG. 2, in an embodiment for a first communitywide care supported by system 212 for mitigating COVID-19 in a target community, one or more non-functional performance measure is formulated and evaluated using one or more metric (e.g., using a confusion matrix) for one or more component (e.g., device, software module, firmware, etc.) of system 212 to determine one or more optimal usage of resources comprising at least one of bandwidth, processing unit (e.g., CPU, GPU, etc.), computability, and combination thereof. In an embodiment, one or more non-functional performance measure for the first communitywide care supported by system 212 is formulated, evaluated, and improved upon (e.g., using one or more metric) to ensure a minimum level of non-functional performance of system 212 (e.g., to meet SLA—system level agreements; maintain validity of system 212; uphold one or more purpose of system 212; etc.) and for continued non-functional performance tuning of system 212 (e.g., to conserve resources, to increase overall life of system 212 and its components, to increase duration between scheduled downtime, to minimize number of unscheduled downtimes, to maintain and enhance disaster-recovery capability, to enhance user accessibility and improve user productivity, etc.); wherein, the system's (212) non-functional performance parameters comprise at least one of: response time (of type, for example, end-to-end, round trip, multiple copy generation—to ensure redundancy and to guarantee disaster-recovery capability—etc.), delivery time (e.g., notification delivery time, voice delivery time, time to receipt of one or more opened notification, etc.), size and pace of content delivery (e.g., to meet a user's expertise and level of training, etc.), and combination thereof.

In FIG. 2, in an embodiment for a first communitywide care supported by system 212 for mitigating COVID-19 in a target community, one or more FPM (functional performance measure)—related to a piece of information comprising at least one of AI-generated intelligence, rule, diagnostic, algorithm, logic in general, and combination thereof, wherein the piece of information is formulated, computed, and generally evaluated with one or more metric—of the first communitywide care supported by system 212 is measured by one or more confusion matrix (as a basis for constructing one or more metric of the one or more FPM) and is supervised by doctor 205. A framework for a first FPM is defined by one or more input from one or more first doctor (and from one or more first administrator in general) to formulate a first metric in the form of a first confusion matrix. The first FPM is applied to operation of the first communitywide care (and system 212) for a first duration of time, wherein outcomes (e.g., predictions, results, diagnoses, etc.) are compared with expectations of the one or more first doctor (and the one or more first administrator in general) to compute the first metric of the first FPM (in the form of the first confusion matrix). Similarly, one or more second duration of time is used to compute one or more second metric of the first FPM as formulated by one or more second doctor (and one or more second administrator in general) in the form of one or more second confusion matrix. One or more third doctor (comprising at least one of the one or more first doctor, the one or more second doctor, doctor 205 in general, the one or more first administrator, the one or more second administrator, one or more administrator of system 212 in general, and combination thereof) analyzes (e.g., compares, contrasts, etc.) the computed first metric (in the form of the first confusion matrix) and the computed one or more second metric (in the form of the one or more second confusion matrix) to gain insights on parameters comprising at least one of: the first FPM; the first metric; the one or more second metric; functionality, viability, and efficacy of system 212 (and the first communitywide care) in general; and combination thereof. The insights allow the one or more third doctor to gain capability comprising at least one of: to improve the first FPM, to develop one or more improved second FPM, to formulate one or more improved fourth metric, to propose improvements to system 212, to propose improvements to the first communitywide care, and combination thereof. Applying the one or more improved second FPM to the operation of the first communitywide care (and system 212) for one or more third duration of time results in formulation and computation of one or more third metric of the one or more improved second FPM. Generally, as compared to the first metric and the one or more second metric, the one or more third metric has improved quality (as it relates to the first communitywide care and system 212) comprising at least one of effectiveness, efficiency, viability, efficacy, fitness for service, and combination thereof. Information (e.g., one or more piece of information) derived from the first metric, the one or more second metric, and the one or more third metric contributes to AI learning (along with developing and updating algorithms, rules, logic, user experience, etc.) associated with the first communitywide care (and system 212).

In FIG. 2 in an embodiment, a first performance measure (of type comprising at least one of: non-functional performance measure, FPM, and combination thereof)—formulated by a first metric—related to a first communitywide care supported by system 212 for mitigating COVID-19 in a target community, allows doctor 205 to assess a first ability of the first communitywide care (and system 212) as a real-time COVID-19 patient monitoring operation. The first ability enables one or more first doctor to increase patient load by an order of magnitude in rendering remote care to COVID-19 patients. The first ability is quantified by an aspect of the first metric—computed as a performance indicator of the first performance measure—in terms of: number of patients monitored by a doctor in a day. Doctor 205 identifies a first KPI (key performance indicator) for the first communitywide care as the average number of patients (remotely monitored) per doctor per day and sets an initial expectation of 100 (average patients per day per doctor) for the first KPI. The first KPI is derived from the first metric—as defined by doctor 205—to assess (system 212 and) the first communitywide care's viability (related to, for example, at least one of: compatibility with a community—e.g., a locality, a region, etc.; resource availability and utilization; fitness for service—e.g., medical, pandemic containment, etc.; and combination thereof) related to a measure of a basis comprising at least one of: economic, jurisdictional, socioeconomic, scientific, business, environmental, and combination thereof. Doctor 205 incorporates into the first metric two prediction classes—low-severity and high-severity (of COVID-19)—as a formulation of the first performance measure. One or more first operation of system 212 is measured for one or more first duration (e.g., for 12 days) for which the first metric is computed to generate a first performance indicator (e.g., an evaluated confusion matrix). The first performance indicator provides doctor 205 with an insight that one more prediction class related to patient noncompliance is needed to improve one or more viability of the first KPI, the first metric, the first performance measure, the first communitywide care, and system 212. Further, the insight about system 212 comprises: to some extent, system 212 may be fault tolerant; system 212 may provide a confidence level for its predictions; system 212 may be aware of instances when it is unable to predict (e.g., it may provide alerts for situations related to insufficient observations and its inability to predict for the situations); and one or more prediction sensitivity related to patient noncompliance may be configured as one or more parameter (comprising at least one of variable, predictor, intelligence, and combination thereof) into system 212 to obtain granular and actionable information (e.g., performance indicators) related to patient noncompliance. In an embodiment, inclusion (in the first metric) of a third class—patient noncompliance—to formulate a second metric to generate a second performance indicator improves the granularity, resolution, and accuracy of the first KPI derived from the second metric (as compared to those derived from the first metric), the first performance measure, the first communitywide care, and system 212.

In FIG. 2, for a first communitywide care supported by system 212 for mitigating COVID-19 in a target community, patients 201 (with low-severity COVID-19) are remotely monitored at their homes. Doctor 205 is concerned about false predictions generated by system 212; doctor 205 hypothesizes that the false predictions are likely due to patient noncompliance. Doctor 205 wants to formulate performance metrics for an FPM of system 212 to gain broad insights and granular reasoning for wrong predictions generated by system 212. For system 212, doctor 205 formulates a confusion matrix (as a metric of the FPM) of three intelligence (related to predictions generated by the AI of system 212) classes: low-severity, high-severity, and patient noncompliance. Low-severity is for low degree of COVID-19 adversity and high-severity is for high degree of COVID-19 adversity. Patient noncompliance represents challenges posed by patients 201 in effective monitoring by system 212 and in attaining optimal efficacy of the first communitywide care. Patients 201, through their actions and inactions, are responsible for the challenges, for example, comprising at least one of: intentional sensor removal (e.g., patients 201 remove sensors associated with data-points 203 or with observations 302 as shown in FIG. 3 for a bathroom break) and unintentional sensor removal (e.g., while sleeping); performing activities (e.g., exercise) which may alter sensor data against the advice of doctor 205; subjecting the sensors to adverse conditions (against the instructions and training provided to patients 201 for use and maintenance of the sensors); and combination thereof.

Figure 4:
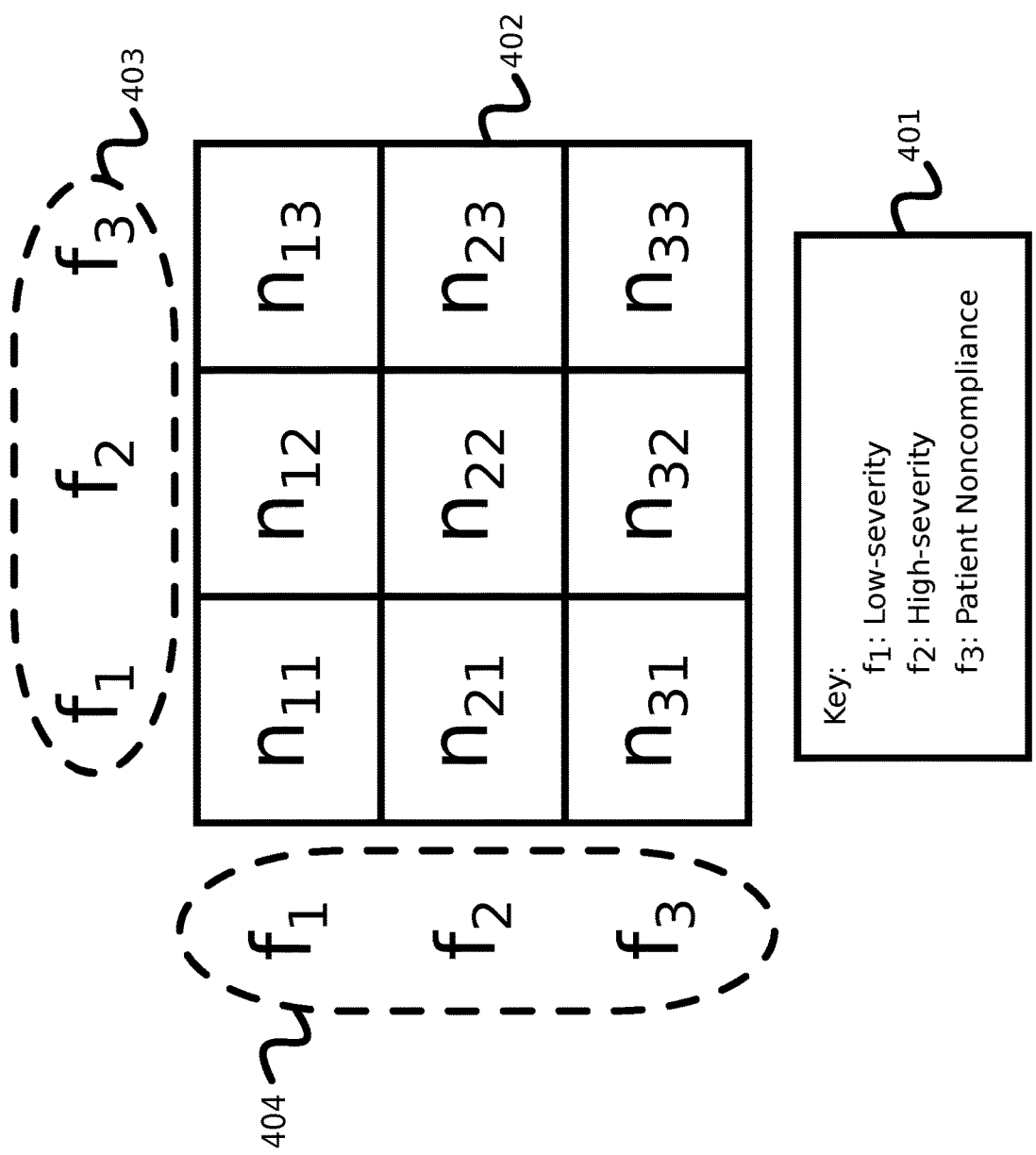
FIG. 4 illustrates a block diagram of a performance measurement process for a communitywide care in accordance with an embodiment of the present application.

FIG. 4 illustrates process 400 in accordance with an embodiment of the present application. FIG. 4 shows confusion matrix 402 used to evaluate the performance of the first communitywide care supported by system 212 (as shown in FIG. 2) for mitigating COVID-19 in the target community by remotely monitoring (e.g., monitoring patients at home) patients 201 with low-severity in the target community. Three classes $f_1$, $f_2$, and $f_3$ that identify the columns of matrix 402 (columns 403) represent prediction classes and are denoted by j. Three classes $f_1$, $f_2$, and $f_3$ that identify the rows of matrix 402 (rows 404) represent truth-value classes (denoted by i). An entry in the matrix 402 at row i and column j is $n_{ij}$, which represents the number of predictions by system 212 (e.g., one prediction per observation in general) with prediction class $f_j$ and truth-value class $f_i$. The 2-tuple $(f_i, f_j)$ represents a truth-value prediction ordered pair. For example, matrix 402 element $n_{21}$ is the number of first predictions where system 212 predicted $f_1$ and the truth-value (for observations corresponding to the first predictions) was $f_2$—represented as $(f_2, f_1)$; system 212 misclassified $n_{21}$ predictions (the first predictions) as $f_1$ while the value expected (for observations corresponding to the first predictions) by doctor 205—the truth-value—was $f_2$. There are $n_{21}$ counts of $(f_2, f_1)$ occurrences. Similarly, system 212 misclassified $n_{13}$ second predictions as $f_3$ while the value expected by doctor 205 was $f_1$—there are $n_{13}$ counts of $(f_1, f_3)$ occurrences. The main diagonal elements of matrix 402 represent counts of third predictions by system 212 that match with expectations (truth-values); for example, system 212 correctly predicted truth-value $f_2$ for $n_{22}$ observations, and there are $n_{22}$ counts of $(f_2, f_2)$ occurrences.

Further in FIG. 4, the classes (403 and 404) are described by Key 401, wherein $f_1$ corresponds to observations of class low-severity; $f_2$, high-severity; and $f_3$, patient noncompliance. In FIG. 2, doctor 205 configures—formulates a first metric of a first FPM of system 212 in the form of a first confusion matrix—matrix 402 in system 212 and remotely and concurrently monitors 50 COVID-19 low-severity home-based patients (patients 201) in real-time. Doctor 205 configures system 212 to generate one prediction per hour (using, for example, an average of predictions over an hour, a prediction based on an average of observations over an hour, and one or more arrangement configured to suit various frequency of observations and various modes of sampling in general) per patient for a 12-day duration (as an average time for COVID-19 progression) corresponding to 14,400 total predictions for the duration. Doctor 205 receives real-time notifications of high-severity onsets, which he diagnoses and examines by initiating communications with system 212 and the related patients. Doctor 205 enters feedback into the system as: $(f_2, f_2)$ for high-severity predictions for true high-severity; $(f_1, f_2)$ for wrong high-severity predictions where low-severity (as truth-values) was expected; and $(f_3, f_2)$ for wrong high-severity predictions where patient noncompliance was detected. Doctor 205, at his convenience (episodically during the 12-day duration and thereafter), reviews $f_1$ (low-severity) class predictions and $f_3$ (patient noncompliance) class predictions generated by system 212 and enters feedback related to $(f_1, f_1)$, $(f_2, f_1)$, $(f_3, f_1)$, $(f_1, f_3)$, $(f_2, f_3)$, and $(f_3, f_3)$, thus completing the first metric (as a performance indicator in the form of a computed instance of the first confusion matrix) for the 12-day period. The first metric is further processed by administrators (doctor 205 and other administrators) of system 212 and the first communitywide care to derive, for the 12-day duration, metrics comprising at least one of: a second metric—total number of true occurrences of low-severity, $n_{11}+n_{12}+n_{13}$; a third metric—total number of true occurrences of high-severity, $n_{21}+n_{22}+n_{23}$; a fourth metric—total number of true occurrences of patient noncompliance, $n_{31}+n_{32}+n_{33}$; a fifth metric—overall prediction accuracy of system 212, $(\Sigma_{i=1}^{3}(n_{ij})_{j=i})/(\Sigma_{i=1}^{3}\Sigma_{j=1}^{3}n_{ij})$; a sixth metric—number of false high-severity alarms $n_{12}+n_{32}$; and combination thereof. Additional metrics that may be calculated comprise at least one of precision, recall, and F1-score for each class. The different metrics generated by system 212 and the administrators (e.g., doctors, engineers, city planners, executives, paramedics, etc.) to compute and formulate the first FPM of system 212 have purposes comprising at least one of: ROI analysis, cost effectiveness estimation, viability (a measure of a basis comprising at least one of economic, social, jurisdictional, scientific, business, environmental, and combination thereof) analysis, reporting of progress in general, planning, forecasting, margin of safety estimation, efficacy analysis, and combination thereof.

In an embodiment, the administrators investigate (e.g., research, hypothesize, verify, etc.) body temperature's relation (e.g., correlations, covariance, biases in general, effects, rules of thumb, etc.) to low-severity and high-severity COVID-19. The administrators incorporate body temperature as a variable in the AI, rules, and logic in general of system 212. Doctor 205 incorporates an additional new class $f_4$—fever: body temperature>100° F.—in formulating a seventh metric (for the first FPM) in the form of a truth table. Doctor 205 further incorporates a fifth class $f_5$—high fever: 104° F.>body temperature>102° F.—in formulating an eighth metric (for the first FPM) in the form of a Bayesian network. The administrators gain one or more insight on relationships among $f_4$ (fever), $f_5$ (high fever), $f_1$ (low-severity), $f_2$ (high-severity), and h (patient noncompliance).

In an embodiment, $f_1$ (low-severity), $f_2$ (high-severity), $f_4$ (fever: body temperature>100° F.) and $f_5$ (high fever: 104° F.>body temperature>102° F.) are thresholds as configured by the administrators; on the other hand, $f_3$ (patient noncompliance) is one or more awareness (as an aspect of a threshold) of system 212 that is acquired (by system 212) by AI learning (of type comprising at least one of online learning, offline learning, transfer learning, and combination thereof). The one or more awareness of system 212 may improve with increased field use and diversity of operations of system 212. Thereafter, in an embodiment, the first communitywide care (and its system 212) transforms into a second multifaceted communitywide care by interfacing (e.g., sharing intelligence and awareness) with one or more communitywide care of different types supported by one or more system. Further, as a result of the interfacing, the first communitywide care improves the one or more awareness ($f_3$, patient noncompliance) to generate one or more improved awareness of a basis comprising at least one of domain awareness, multi-domain awareness, global awareness, and combination thereof.

In an embodiment, the administrators of system 212 (and the associated first communitywide care) and a first entity—comprising at least one of: administrators, experts, awareness machines and AI in general, systems, and combination thereof—investigate and compensate for (e.g., analyze, formulate, and overcome in general) one or more challenges (for example, operational difficulties, hidden variables in models, accidents and their recurrences, etc.) to the first communitywide care and system 212 due to one or more defect of a basis comprising at least one of: patient noncompliance, downtime, connectivity and resource (comprising at least one of power, network, broadband, compute, and combination thereof) interruption, equipment malfunction, and combination thereof. The investigation and compensation employ techniques comprising at least one of: increasing dimensionality and resolution (of, for example, observations, data, analysis, communication, etc.), identifying hidden variables (by, for example, hypothesizing, testing, verifying, etc.), improving awareness in general, improving nuances of intelligence, tuning in general, employing redundancy and recovery (e.g., disaster recovery, backup recovery, etc.), and combination thereof.

In an embodiment, doctor 205 (as shown in FIG. 2) increases dimensionality (to improve, for example, awareness of system 212, granularity of observation, and nuances of information as an enhancement to intelligence) of a ninth metric (e.g., a confusion matrix) by incorporating factors comprising at least one of confidence levels, urgency levels, and combination thereof. In an embodiment, a multidimensional metric of a globally aware system may impart on the globally aware system one or more artificial intelligence (AI) aspect comprising at least one of: intelligence resembling cognitive AI, intelligence approaching cognitive AI, intelligence at par with cognitive AI, and combination thereof.

In an embodiment, one or more tenth metric formulated for a second performance measure (comprising at least one of non-functional performance measure, FPM, and combination thereof) derived from an older version of system 212 is analyzed by designers, developers, and testers of system 212 to add and improve functional and non-functional features to create a subsequent newer version of system 212. One or more performance improvement (related to the second performance measure) of the older version of system 212 may be of type comprising at least one of: online and offline fine-tuning, online and offline learning of AI, online and offline updating of rules and logic, scaling up and down of the system footprint, optimizing resource utilization, increasing user accessibility and intuitiveness (of system 212 and its related communitywide care), and combination thereof. In an embodiment, a first operation related to a first system may be online in general if the first operation is executed during a field operation (of type, for example, comprising at least one of: full production level, reduced production level, field testing, beta testing, and combination thereof) of the first system; online execution may also be known as hot execution or live execution, among others. A second operation related to a second execution of a second system may be offline in general if the second execution is carried out during a period comprising at least one of: downtimes (e.g., planned, unplanned, etc.), before a field deployment of the second system, lab testing (e.g., with test data, alpha testing, etc.), and combination thereof. A third operation related to a third system may be a combination of the first operation and the second operation, wherein the third operation—depending on the extent of online and offline execution—may be regarded as either online or offline. Examples of the third operation are redundant activities (e.g. activity modes comprising at least one of active-active, active-passive, standby, backup ready, and combination thereof), failovers, disaster recovery activities, and combinations thereof.

In an embodiment for a first communitywide care related to COVID-19, one or more threshold may be of type comprising at least one of temperature level, oxygen level, heart rate, respiratory rate, rate of change, acceleration (and related higher order derivatives of change), and combination thereof. In an embodiment of a second communitywide care related to autonomous driving, one or more threshold may be of type comprising at least one of speed, visibility, following distance, clearance from side (e.g., curb, railing, etc.), fuel level, braking distance, maintenance in general, traffic flow, traffic density in general, and combination thereof. In an embodiment for a third communitywide care related to one or more infrastructure, one or more threshold may be of type comprising at least one of area, weight, volume, voltage, current, energy in general, pressure, temperature, density, bandwidth, throughput, rate of change, acceleration (and related higher order derivatives of change), and combination thereof. The one or more infrastructure may be of type comprising at least one of: utility services (e.g., electric, water, gas, internet, satellite service, etc.); delivery and transportation services (related to, for example, routes of road, rail, water, and air ways); industrial infrastructures (of type, for example, comprising at least one of exploration (e.g., oil and gas), development, production, agriculture, processing, internet and cyber, maintenance, servicing and combination thereof); city and locality services; and combination thereof. In general, one or more threshold (for, for example, the first communitywide care, the second communitywide care, the third communitywide care, and combination thereof) may be of type comprising at least one of confidence level, noncompliance extent, priority, urgency level, rate of change in general, acceleration (and related higher order derivatives of change) in general, and combination thereof.

Figure 5:
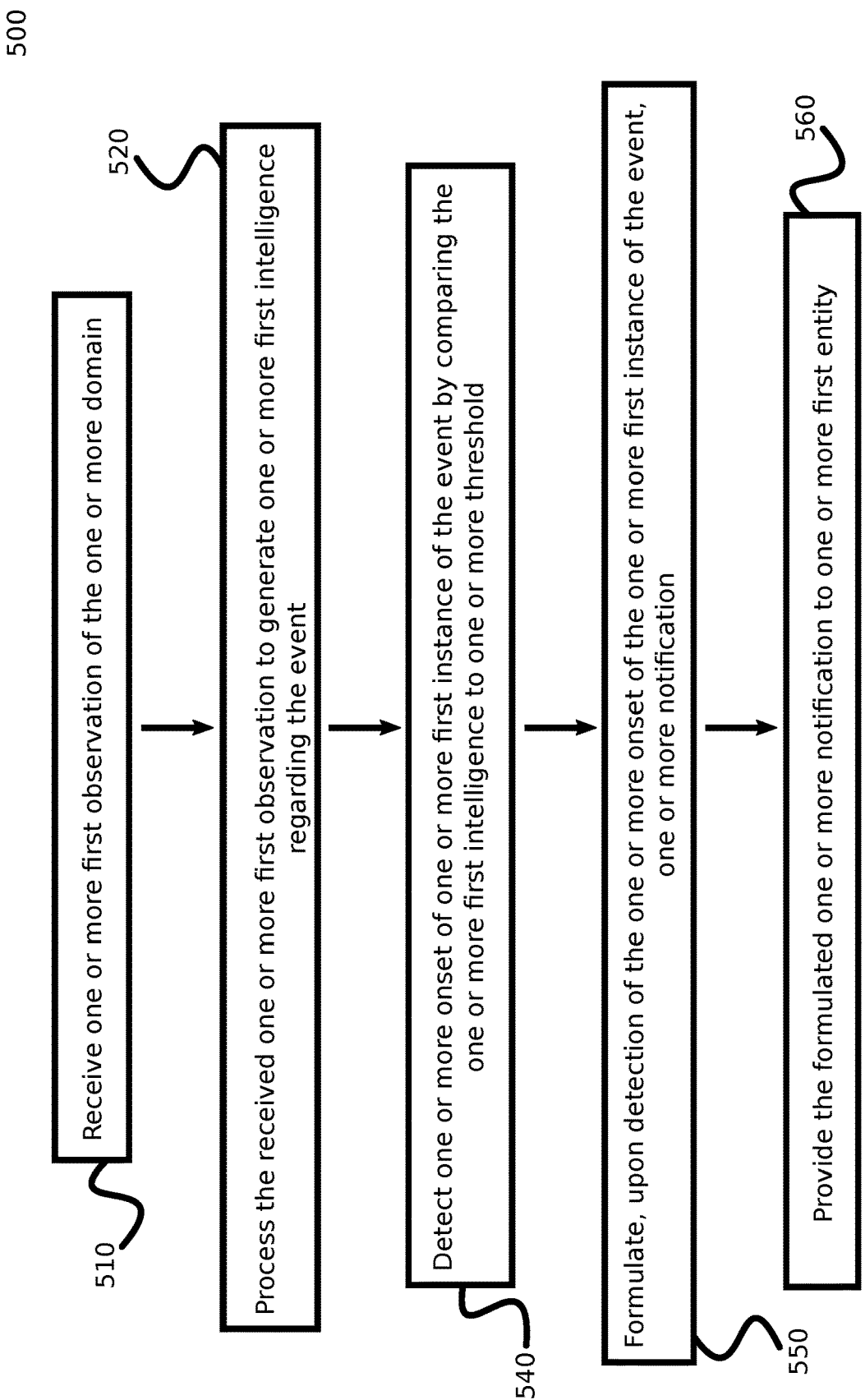
FIG. 5 illustrates a flow diagram of a method in accordance with an embodiment of the present application.

FIG. 5 illustrates a method 500 in accordance with an embodiment of the present application. In certain embodiments, method 500 may correspond to the process—of a first communitywide care, which computes its one or more intelligence with one or more metric—described with reference to FIGS. 1-4 related to remote monitoring for an event of one or more domain. At block 510, method 500 includes receiving one or more first observation of the one or more domain. At block 520, method 500 includes processing the received one or more first observation to generate one or more first intelligence regarding the event; wherein, the one or more first intelligence may be a first computation of a first metric. At block 540, method 500 includes detecting one or more onset (which may be characterized by one or more computation of the first metric) of one or more first instance of the event by comparing the one or more first intelligence to one or more threshold. At block 550, method 500 includes formulating, upon detection of the one or more onset of the one or more first instance of the event, one or more notification. At block 560, method 500 includes providing the formulated one or more notification to one or more first entity. The comparing (of the one or more first intelligence to the one or more threshold) and its corresponding detection (of the one or more onset of the one or more first instance of the event) is a first indicator of the first communitywide care. In an embodiment, an evaluation of a parameter comprising at least one of: a metric, the metric's one or more computation, and combination thereof, with respect to a threshold (of type comprising at least one of: an expectation, a prior, a convention, a mandate, a predetermined structure in general, a dynamic structure in general, and combination thereof) may be marked, used, and otherwise referred to as an indicator of a basis comprising at least one of: a detection, an onset, an event, a part of a snapshot, an intelligence, a piece of information in general, and combination thereof. The evaluation comprises at least one of: comparison, gradation, classification, clustering, demarcation, cognitive assessment (e.g., making a calculated guess, generating and applying inference, hypothesizing, etc.), and combination thereof.

In an embodiment, method 500 may include receiving one or more second observation of the one or more domain; processing the received one or more second observation along with one or more second piece of information comprising at least one of: the one or more first observation, the one or more first intelligence, a plurality of third intelligences, one or more first awareness, a plurality of second awareness, and combination thereof to generate one or more second intelligence regarding the event; detecting—as a second indicator—one or more second onset of one or more second instance of the event by comparing the one or more second intelligence to the one or more threshold; formulating, upon detection of the one or more second onset of the one or more second instance of the event, one or more second notification; and providing the formulated one or more second notification to one or more second entity.

In an embodiment, method 500—of the first communitywide care supported by one or more first system—as it relates to the one or more first observation, may include—as a first step (wherein the term "first" of the first step is a notation and may not be an aspect of a sequence)—exchanging, of the one or more first system with one or more second system (with corresponding one or more second communitywide care), one or more fourth piece of information comprising at least one of: one or more fourth intelligence, one or more fourth awareness, one or more fourth data, the one or more first observation, the one or more first intelligence, and combination thereof; wherein, the one or more fourth piece of information may be a fourth computation of a fourth metric. At block 540, method 500 may be enhanced to include detecting—as a fourth indicator—one or more fourth onset (which may be characterized by one or more computation of the fourth metric) of the one or more first instance of the event by comparing the one or more fourth piece of information to one or more fourth threshold (which, for example, may be more rich, comprehensive, complex, and nuanced than the one or more threshold). At block 550, method 500 may include formulating, upon detection of the one or more fourth onset of the one or more first instance of the event, one or more fourth notification. At block 560, method 500 may include providing the formulated one or more fourth notification to one or more fourth entity. The enhanced detection at block 540, due to the first step, may upgrade the first communitywide care (associated with method 500) to a multifaceted communitywide care. The first step may improve, for the one or more first instance of the event (corresponding to the one or more first observation), the detecting (the fourth indicator) of the one or more fourth onset over the detecting (the first indicator) of the one or more onset. The improvement is of type comprising at least one of: higher accuracy, efficacy, and effectiveness of the corresponding onset, its detection, related metric (e.g., improvement of the first metric to generate the fourth metric that is more capable with respect to the first communitywide care), and related performance measure; better quality of intelligence (e.g., the more rich, granular, actionable, and nuanced fourth metric versus the first metric) for the first communitywide care and the one or more first system; greater awareness for the one or more first system; and combination thereof. The one or more onset may be represented by the first metric, while the one or more fourth onset may be represented by one or more fourth metric.

In an embodiment, method 500 may include a third step (wherein the term "third" of the third step is a notation and may not be an aspect of a sequence), wherein consolidating (e.g., distilling from one or more piece of information, extracting essence of one or more piece of information, etc.) one or more fifth piece of information (comprising at least one of: the fourth piece of information, the one or more second piece of information, the one or more second observation, of the event, of the one or more domain, of the one or more first system, and combination thereof), results in the one or more first system attaining one or more fifth awareness comprising at least one of: of the one or more onset of the one or more first instance of the event, of the one or more fourth onset of the one or more first instance of the event, of the one or more second onset of the one or more second instance of the event, of the one or more first instance of the event, of the one or more second instance of the event, of the event, of the one or more domain, of the one or more first system, and combination thereof; wherein, the one or more fifth piece of information is a fifth computation (e.g., an awareness message) of a fifth metric. The one or more fifth awareness is characterized by nuances of a basis comprising at least one of: diversity of information, diversity of source of information, redundancy of information, redundancy of source of information, frequency of information, recurrence (or lack thereof) of information, and combination thereof. In an embodiment, the nuances represent higher-order knowledge (e.g., knowledge of knowledge, metadata in general, knowledge as a tool to generate new knowledge, learning to learn, etc.) as an aspect of the one or more fifth awareness. At block 540, method 500 may be enhanced to include detecting (as a fifth indicator) one or more fifth onset of the one or more first instance of the event based on the one or more fifth awareness. At block 550, method 500 may include formulating, upon detection of the one or more fifth onset of the one or more first instance of the event, one or more notification. At block 560, method 500 may include providing the formulated one or more notification to one or more fifth entity. The enhanced detection at block 540 is due to the one or more fifth awareness of the one or more first system. In an embodiment, the one or more fifth entity may receive (e.g., as provided by the one or more first system) the one or more fifth awareness to attain one or more sixth awareness comprising at least one of: of the one or more onset of the one or more first instance of the event, of the one or more second onset of the one or more second instance of the event, of the one or more fourth onset of the one or more first instance of the event, of the one or more fifth onset of the one or more first instance of the event, of the one or more first instance of the event, of the one or more second instance of the event, of the event, of the one or more domain, of the first communitywide care, of the one or more first system, and combination thereof.

In an embodiment, method 500 that is related to the first communitywide care is supported by the one or more first system, wherein the one or more first system has attained one or more seventh awareness. The first communitywide care and the one or more first system may be overseen (e.g., administered, operated, orchestrated, etc.) by a seventh entity comprising at least one of: an administrator, the one or more first system that has attained the one or more seventh awareness, one or more eighth system that has attained one or more eighth awareness, and combination thereof.

In certain embodiments, at block 510 "one or more first observation", and at block 520 "the received one or more first observation", may represent "a plurality of first observations" and "the received plurality of first observations", respectively. In certain embodiments, at block 520 "one or more first intelligence", and at block 540 "the one or more first intelligence", may represent "a plurality of first intelligences" and "the plurality of first intelligences", respectively. In certain embodiments, at block 540 "one or more first instance", and at block 550 "the one or more first instance", may represent "a plurality of first instances" and "the plurality of first instances", respectively. In certain embodiments, at block 540 "one or more onset", and at block 550 "the one or more onset", may represent "a plurality of onsets" and "the plurality of onsets", respectively. In certain embodiments, at block 560 "one or more first entity" may represent "a plurality of first entities".

In certain embodiments, at block 540 "one or more threshold" may represent "a plurality of thresholds". In an embodiment, a plurality of thresholds is of a basis comprising at least one of: distributions (distributions of, for example, random copolymers, block copolymers, DNA sequences, etc.), time sequences (e.g., daily movements of a liquid security in a market—commodity market, stock market, etc.), boundaries (boundaries of, for example, flood plains, cancerous cell masses, comfort zones in general, etc.).

Figure 6:
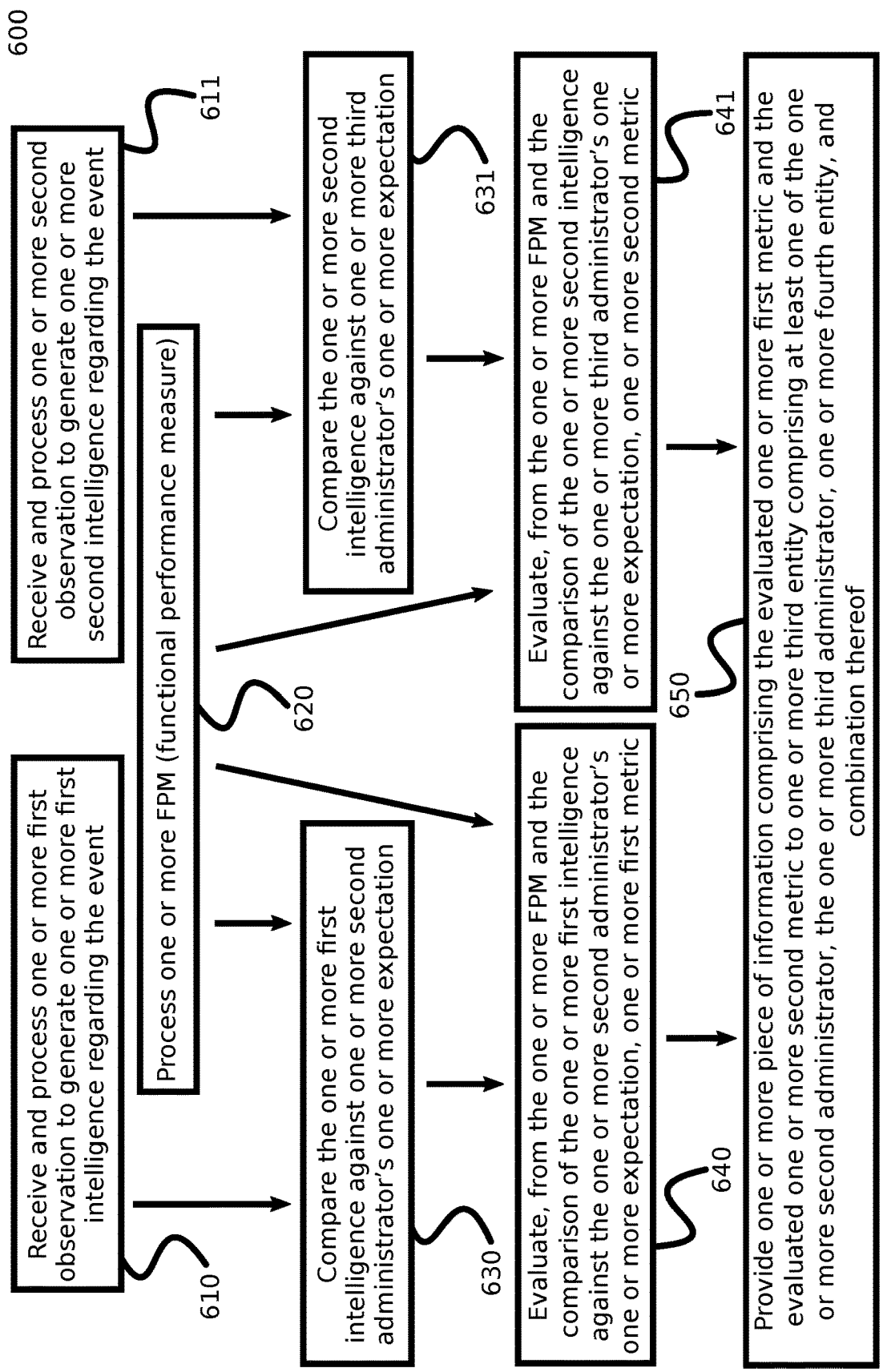
FIG. 6 illustrates a flow diagram of a method in accordance with an embodiment of the present application.

FIG. 6 illustrates a method 600 in accordance with an embodiment of the present application. In certain embodiments, method 600 may correspond to the process described with reference to FIGS. 1-5 related to remote monitoring for an event of one or more domain. At block 610, method 600 includes receiving and processing one or more first observation to generate one or more first intelligence regarding the event. At block 611, method 600 includes receiving and processing one or more second observation to generate one or more second intelligence regarding the event. At block 620, method 600 includes processing one or more FPM (functional performance measure). In an embodiment, block 610 and block 611 may represent receiving and processing a plurality of observations (or one or more fourth observation) to generate a plurality of intelligences.

At block 630, method 600 includes comparing the one or more first intelligence against one or more second administrator's one or more expectation. At block 631, method 600 includes comparing the one or more second intelligence against one or more third administrator's one or more expectation. In an embodiment, block 630 and block 631 may represent comparing the plurality of intelligences against a plurality of expectations (or one or more fourth expectation) of a plurality of fourth administrators (or one or more fifth administrator).

In an embodiment, a plurality of entities (e.g., a crowd, a swarm, etc.) participating in one or more crowdsourcing effort may represent the plurality of fourth administrators. In an embodiment, the plurality of expectations (or the one or more fourth expectation) of the plurality of fourth administrators and the plurality of entities may represent one or more collective wisdom (e.g., wisdom of crowds, one or more awareness of crowds, swarm behavior, collective behavior in general, etc.); the one or more collective wisdom may represent the plurality of fourth administrators' and the plurality of entities' one or more fifth intelligence (or a plurality of fifth intelligences) of a basis comprising at least one of: altruism, greed, selfishness, coordination, incoordination, cooperation, noncooperation, synergism, competition, opposition, dispute, adversarial behaviors, cognition and cognitive behaviors (e.g., thinking, judging, social activities, one or more emotion, actions rooted in one or more emotion, etc.), and combination thereof.

At block 640, method 600 includes evaluating, from the one or more FPM and the comparison of the one or more first intelligence against the one or more second administrator's one or more expectation, one or more first metric. At block 641, method 600 includes evaluating, from the one or more FPM and the comparison of the one or more second intelligence against the one or more third administrator's one or more expectation, one or more second metric. In an embodiment, block 640 and block 641 may represent evaluating, from the one or more FPM and the comparisons of the plurality of intelligences against the plurality of expectations (or the one or more fourth expectation), a plurality of metrics (or one or more fourth metric).

In an embodiment, the one or more first metric and the one or more second metric formulate the one or more FPM; one or more computation of the one or more first metric and the one or more second metric may represent one or more indicator related to the one or more FPM for the remote monitoring of the event of the one or more domain (e.g., for one or more communitywide care related to method 600 that is supported by one or more system). In an embodiment, the plurality of metrics (or the one or more fourth metric) may formulate the one or more FPM; a plurality of computations (or one or more fourth computation) of the plurality of metrics (or the one or more fourth metric) may represent a plurality of indicators (or one or more fourth indicator) related to the one or more FPM for the remote monitoring of the event of the one or more domain (e.g., for one or more communitywide care related to method 600 that is supported by one or more system).

At block 650, method 600 includes providing one or more piece of information comprising the evaluated one or more first metric and the evaluated one or more second metric to one or more third entity comprising at least one of: the one or more second administrator, the one or more third administrator, one or more fourth entity, and combination thereof. In an embodiment, the one or more piece of information—in addition to the evaluated one or more first metric and the evaluated one or more second metric—comprises at least one of the one or more first metric, the one or more second metric, the one or more FPM, the one or more first observation, the one or more second observation, the one or more first intelligence, the one or more second intelligence, one or more peripheral piece of information, and combination thereof; wherein, the one or more peripheral piece of information is of a basis comprising at least one of economic, social, jurisdictional, scientific, business, environmental, and combination thereof. In an embodiment, block 650 represents providing the evaluated plurality of metrics (or the evaluated one or more fourth metric) to one or more fifth entity comprising at least one of: the plurality of fourth administrators (or the one or more fifth administrator), one or more sixth entity, and combination thereof.

At block 650, for method 600, providing the one or more piece of information to the one or more third entity may enable the one or more third entity to gain one or more insight comprising at least one of: effectiveness of one or more second system related to method 600, effectiveness of one or more second communitywide care related to method 600, efficacy of the one or more second system, efficacy of the one or more second communitywide care, performance and viability in general of the one or more second system, performance and viability in general of the one or more second communitywide care, improvements for the one or more FPM to enable construction of a subsequent improved one or more second FPM, and In an embodiment, at block 650, for method 600, providing the evaluated plurality of metrics (or the evaluated one or more fourth metric)—which may be accompanied by one or more piece of information comprising at least one of: the one or more FPM, the plurality of metrics or the one or more fourth metric, the plurality of observations or the one or more fourth observation, the plurality of intelligences, the one or more peripheral piece of information, and combination thereof—to the one or more fifth entity may enable the one or more fifth entity to gain one or more insight comprising at least one of: effectiveness, efficacy, performance and viability in general, and combination thereof, of one or more third system related to method 600 and one or more third communitywide care related to method 600.

In an embodiment, for method 600, the one or more first observation is processed into the one or more first metric, the one or more second observation is processed into the one or more second metric, and the plurality of observations (or the one or more fourth observation) is processed into the plurality of metrics (or the one or more fourth metric)—e.g., for one or more communitywide care that is supported by one or more system related to method 600.

In an embodiment, for method 600 related to one or more communitywide care, the one or more first intelligence may be one or more first awareness of one or more first system that supports the one or more communitywide care, and the one or more second intelligence may be one or more second awareness of one or more second system that supports the one or more communitywide care; wherein, the resulting one or more insight gained by the one or more third entity may improve (e.g., due to one or more beneficial aspect of awareness). In an embodiment, for method 600 related to one or more communitywide care, the plurality of intelligences may be a plurality of awareness of one or more third system that supports the one or more communitywide care; wherein, the resulting one or more insight gained by the one or more fifth entity may improve (e.g., due to one or more beneficial aspect of awareness).

In an embodiment, for method 600 related to one or more multifaceted communitywide care, the multifaceted aspect of the one or more multifaceted communitywide care improves the one or more first intelligence (generating one or more enhanced version of the one or more first intelligence) and the one or more second intelligence (generating one or more enhanced version of the one or more second intelligence); wherein, the resulting one or more insight gained by the one or more third entity may improve (e.g., due to one or more beneficial aspect of multifaceted communitywide cares). In an embodiment, for method 600 related to one or more multifaceted communitywide care, the multifaceted aspect of the one or more multifaceted communitywide care improves the plurality of intelligences (generating one or more enhanced version of the plurality of intelligences); wherein, the resulting one or more insight gained by the one or more fifth entity may improve (e.g., due to one or more beneficial aspect of multifaceted communitywide cares).

In an embodiment, for method 600, a first system related to method 600 processes the one or more first observation into the evaluated one or more first metric, and a second system related to method 600 processes the one or more second observation into the evaluated one or more second metric. Thereafter, for method 600, providing one or more piece of information comprising the evaluated one or more first metric and the evaluated one or more second metric to the one or more third entity enables the one or more third entity to gain one or more second insight comprising at least one of: effectiveness of the first system, effectiveness of the second system, relative effectiveness of the first system versus the second system, efficacy of the first system, efficacy of the second system, relative efficacy of the first system versus the second system, performance and viability (e.g., a measure of a basis comprising at least one of economic, social, jurisdictional, scientific, business, environmental, and combination thereof) in general of the first system, performance and viability in general of the second system, relative performance and viability in general of the first system versus the second system, and combination thereof.

In an embodiment, method 600 may be related to one or more multifaceted communitywide care. At block 610, method 600 may include receiving and processing one or more first observation to generate one or more first enhanced intelligence (e.g., related to enhanced detection) regarding the event. At block 611, method 600 includes receiving and processing one or more second observation to generate one or more second enhanced intelligence regarding the event. At block 620, method 600 may include processing one or more FPM (functional performance measure). At block 630, method 600 may include comparing the one or more first enhanced intelligence against one or more second administrator's one or more expectation. At block 631, method 600 may include comparing the one or more second enhanced intelligence against one or more third administrator's one or more expectation. At block 640, method 600 may include evaluating, from the one or more FPM and the comparison of the one or more first enhanced intelligence against the one or more second administrator's one or more expectation, one or more first metric. At block 641, method 600 may include evaluating, from the one or more FPM and the comparison of the one or more second enhanced intelligence against the one or more third administrator's one or more expectation, one or more second metric. At block 650, method 600 may include providing one or more piece of information comprising the evaluated one or more first metric and the evaluated one or more second metric to one or more third entity comprising at least one of: the one or more second administrator, the one or more third administrator, one or more fourth entity, and combination thereof. At block 650, for method 600, providing the one or more piece of information may enable the one or more third entity to gain one or more enhanced insight related to the one or more multifaceted communitywide care. In an embodiment, a multifaceted communitywide care may be an enhanced version of a first communitywide care, whereby an intelligence generated by the multifaceted communitywide care may be an enhanced version of the corresponding intelligence generated by the first communitywide care; a detection of an onset of an instance of the event by the multifaceted communitywide care may be an enhanced version of the corresponding detection by the first communitywide care. For the one or more third entity, one or more insight gained due to the multifaceted communitywide care may be an enhanced version of the corresponding one or more insight gained due to the first communitywide care.

In an embodiment, method 600—in relation to the remote monitoring for the event of the one or more domain—may be related to one or more system that has attained one or more awareness. In general, the one or more awareness is characterized by nuances of a basis comprising at least one of: diversity of information, diversity of source of information, redundancy of information, redundancy of source of information, frequency of information, recurrence (or lack thereof) of information, and combination thereof. In an embodiment, the nuances represent higher-order knowledge (e.g., knowledge of knowledge, metadata in general, knowledge as a tool to generate new knowledge, learning to learn, etc.) as an aspect of the one or more awareness. At block 610, method 600 may include receiving and processing one or more first observation to generate one or more first enhanced intelligence regarding the event and to generate one or more first awareness (e.g., in the form of an awareness message) comprising at least one of: of one or more onset of one or more first instance of the event, of the one or more first instance of the event, of the event, of the one or more domain, and combination thereof. At block 611, method 600 may include receiving and processing one or more second observation to generate one or more second enhanced intelligence regarding the event and to generate one or more second awareness (e.g., in the form of an awareness message) comprising at least one of: of one or more onset of one or more second instance of the event, of the one or more second instance of the event, of the event, of the one or more domain, and combination thereof. At block 620, method 600 may include processing one or more FPM (functional performance measure) designed for evaluating (comprising at least one of comparing, computing, grading, classifying, and combination thereof) awareness (e.g., in the form of an awareness message) and associated enhanced intelligence. At block 630, method 600 may include comparing the one or more first awareness against one or more second administrator's one or more expectation. At block 631, method 600 may include comparing the one or more second awareness against one or more third administrator's one or more expectation. At block 640, method 600 may include evaluating, from the one or more FPM and the comparison of the one or more first awareness against the one or more second administrator's one or more expectation, one or more first metric. At block 641, method 600 may include evaluating, from the one or more FPM and the comparison of the one or more second awareness against the one or more third administrator's one or more expectation, one or more second metric. At block 650, method 600 may include providing one or more piece of information comprising the evaluated one or more first metric and the evaluated one or more second metric to one or more third entity comprising at least one of: the one or more second administrator, the one or more third administrator, one or more fourth entity, and combination thereof. At block 650, for method 600, providing the one or more piece of information to the one or more third entity may enable the one or more third entity to gain one or more insight comprising at least one of: effectiveness of the one or more system, effectiveness of a first communitywide care related to method 600 and the one or more system, efficacy of the one or more system, efficacy of the first communitywide care, performance and viability (e.g., a measure of a basis comprising at least one of economic, social, jurisdictional, scientific, business, environmental, and combination thereof) in general of the one or more system, performance and viability in general of the first communitywide care, one or more improvement for the one or more FPM to enable construction of a subsequent improved one or more second FPM, and combination thereof. In an embodiment, the one or more third entity may receive (e.g., as provided by the one or more system), the one or more first awareness and the one or more second awareness to attain one or more third awareness comprising at least one of: of the one or more onset of the one or more first instance of the event, of the one or more first instance of the event, of the one or more onset of the one or more second instance of the event, of the one or more second instance of the event, of the event, of the one or more domain, of the one or more system, and combination thereof. In an embodiment, the one or more piece of information—in addition to the evaluated one or more first metric and the evaluated one or more second metric—comprises at least one of the one or more first metric, the one or more second metric, the one or more FPM, the one or more first observation, the one or more second observation, the one or more first enhanced intelligence, the one or more second enhanced intelligence, the one or more first awareness, the one or more second awareness, one or more peripheral piece of information, and combination thereof; wherein, the one or more peripheral piece of information is of a basis comprising at least one of economic, social, jurisdictional, scientific, business, environmental, and combination thereof.

In an embodiment, one or more communitywide care may have an objective (comprising at least one of: monitoring, preventing, mitigating, performance tuning and fault tolerance, and combination thereof) in overcoming one or more adversity (for example, disaster, accident, deficiency, inefficiency, and combination thereof) of type comprising at least one of: environmental, shortage, wastage, natural disaster, social disturbance, process induced (related to, for example, supply chain, distribution, procurement, fulfillment, and combination thereof of one or more product, one or more service, and combination thereof), and combination thereof. In an embodiment, the one or more communitywide care may relate to (in a manner comprising at least one of:

real-time, on-demand, episodic, and combination thereof) an aspect of autonomous driving comprising at least one of: infrastructure (for example, for fueling, maintenance, short term parking, and long term storage); navigation (for example, path mapping, traffic congestion avoidance, toll avoidance, and minimizing time to destination); safety (of, for example, drivers, passengers, pedestrians, pets, wildlife, property, and the autonomous vehicle itself); directives and guidance (e.g. jurisdiction, bylaws, acceptable loss for one or more situation at hand, unavoidable damage, traffic coordination, and policy in general); awareness; prohibitions (e.g. restrictions, counter mandates); precautions; remediation; and combination thereof. In an embodiment, the one or more communitywide care may relate to infrastructure (e.g. electric grid, supply and refueling, utility provisioning, etc.). In an embodiment, the one or more communitywide care may relate to behaviors comprising at least one of: sentiment, cognitive and collective actions, swarm behaviors, crowd dynamics, and combination thereof of a community comprising at least one of: locality, city, organization, crowd, swarm, social media and online groups, markets (e.g., financial, housing, wholesale and retail, etc.), and combination thereof.

In an embodiment, a first system may generate one or more intelligence in response to an event (e.g., high-severity), wherein the one or more intelligence is in the form of a second system (e.g., an AI, an AI system, etc.) created (e.g., induced, conceived, developed, improved, deployed, and combination thereof) by the first system. Thereafter, one or more response (e.g., of type comprising at least one of prediction, intelligence, alert, message, report, record, and combination thereof) to the event and one or more observation of the event may be coordinated (e.g., orchestrated, contributed to, administered, generally helped, etc.) by at least one of: the first system, a part of the first system, the second system, a part of the second system, and combination thereof. In an embodiment, the second system may be a subsystem (e.g., a component, a part, a module, etc.) of the first system.

In an embodiment, severity may be related to a loss, comprising at least one of: damage, injury, pain, cost, demise, death, deficit, deficiency, shortfall, missed gain, missed opportunity, missed advantage in general, failure, defeat, and combination thereof. A loss may be of a basis comprising at least one of: resource, wealth, energy, viability, vitality, efficiency, knowledge, skill, ability, agency (e.g., the domain manipulation capability), social or group status, reputation and social standing, approval in general, and combination thereof. A loss may be due to one or more actor's activities comprising at least one of: speculation, mistake, error, representation, communication, planning, inaction, action in general, and combination thereof. Other reasons for a loss are one or more cause comprising at least one of: natural, manmade, intentional, unintentional, planned, accidental, inevitable, avoidable, and combination thereof.

In an embodiment of the present application, one or more process of persistence of a piece of information (of type comprising at least one of data-point; observation; intelligence; a system's state comprising at least one of conception, architecture, design, operation, testing, recovery, and combination thereof; domain information; awareness; planning; speculation; information in general, and combination thereof) may take place at any step (e.g., an instance of time, logical demarcation, compartment in general, etc.) after an instantiation (of type comprising at least one of: by receiving, by generating, by retrieving, by repossessing, and combination thereof) of the piece of information.

In an embodiment, AI may be an artificial neural network (ANN). An ANN may comprise at least one of various configurations; by way of example, and not limitation, a configuration may be altered by altering the number of hidden layers or depth configuration. An ANN may be of a basis comprising at least one of: static, temporal, generative, generative-adversarial, reinforcement learning, and combination thereof. A temporal ANN may be of a basis comprising at least one of discrete, continuous, time-delayed, synchronous, asynchronous, and combination thereof. As an aspect of AI, reinforcement learning—both online and offline—may be utilized for Markov decision processes, their derivatives, and non-Markovian processes.

In certain embodiments, the term "learning" refers to training of artificial intelligence (AI). In an embodiment, the training may be of type comprising at least one of: supervised, unsupervised, generative, generative adversarial, reinforcement (both online learning and offline learning), active or query learning (e.g., where the learning mechanism is designed to choose certain learning samples over others), and combination thereof. Reinforcement learning—e.g., goal-directed, decision making, and/or planning-based—of systems may be done by learning comprising at least one of: policy learning, reward learning, value function learning, and combination thereof. The learning of the model of the environment in its entirety may not be needed (e.g., in hidden-mode Markov decision processes). Genetic algorithms and annealing may be used either independently of, or in combination with, the learning methods. In an embodiment, an AI of a system (e.g., supporting a communitywide care), as part of its operation or its learning in general, may use forgetting as a method or as a skill to increase efficiency and effectiveness, improve efficacy, and to generally advance goals of one or more beneficiary.

In an embodiment, generation of labeled learning data for a system (e.g., supporting a communitywide care) may be specific to an aspect comprising at least one of: domain, event, actor, efficacy requirement, performance measure in general, and combination thereof. Depending on an AI and the learning techniques, there may be specific techniques of input data preprocessing (e.g., normalization, flattening, and centering) that may affect the performance of the AI. In an embodiment, for a duration of an event, one or more first observation may represent one or more input for one or more prediction. In an embodiment, one or more (truth-value, prediction) ordered pair—e.g., in FIG. 4, the 2-tuples $f_1$, $f_2$), ($f_2 f_2$), ($f_3$, $f_1$), etc.—corresponding to one or more observation may represent one or more labelled data.

In an embodiment, artificial intelligence (AI) learning is of type comprising at least one of: linear regression, support vector machines, graphical models (comprising at least one of Markov networks, Markov chains, Bayesian networks, and combination thereof), probabilistic inference, time series based, neural networks, clustering, and combination thereof. In an embodiment, AI systems may also comprise at least one of: expert systems, rules engines, inference engines, semantic reasoners, and other systems capable of processing higher-order representations as well as higher-order logic.

It is noted that marks and identifiers used in black-and-white FIGS. 1-6 may be represented in different colors; the marks and identifiers may comprise at least one of: symbols, keys or legends, text notations, hatching and shading, a floor-plan, or the like. Figures that are embodiments of user interfaces, user interactions, and user communication in general—e.g., displays of a smartphone, an augmented-reality device, or other device—may be representations of colored displays. There may be other ways to display the same user information comprising at least one of: different languages, symbols, notations, conventions, and representations. In an embodiment, the user information may be governed by the rules and regulations of the concerned jurisdiction.

As used herein, the phrase "comprising at least one of" (and similarly, the phrase "comprises at least one of") for a first list is referred broadly to mean: a second list equivalent to "at least one of a list comprising the first list" inclusive of combinations, and "comprising a list of at least one of the first list" inclusive of combinations. For example, a first list of letters is "A, B, and C" and a second list of letters—equivalent to comprising at least one of the first list—may include one or more of: one or more A, one or more B, one or more C, one or more D, one or more Z, and one or more of all combinations of A, B, C, D, and Z.

In certain embodiments, the phrase "one or more" indicating a count may optionally signify "a plurality of" indicating a form comprising at least one of: count, ensemble, distribution, collection in general, and combination thereof; for example, "one or more" may optionally mean "one or more, or a plurality of"; and "one or more of" may optionally mean "one or more of, or a plurality of". In an embodiment, "a plurality of" may be regarding a generally mathematical representation comprising at least one of: ensemble (e.g., statistical ensemble; ensemble in frequentist probability analysis; ensemble in Bayesian model averaging; ensemble in Bayes classifiers; ensemble in learning algorithms comprising bagging, boosting, stacking, bucket of models, and model averaging; etc.), prior (e.g., as it relates to Bayes theorem, as it relates to inference, a prior probability distribution, etc.), posterior (e.g., as it relates to Bayes theorem, as it relates to inference, a posterior probability distribution, etc.), distribution (e.g., for probability distribution, for uncertainty estimation, for likelihood analysis, etc.), graph (e.g., networks, node-edge structures, maps, etc.), complex grouping (e.g., swarm; dynamic collective; complex presentations of a basis comprising at least one of: self-reference, circular-reference, ergodic-reference, and combination thereof), peer-to-peer collective (e.g., peer-to-peer network, peer-to-peer communication, peer-to-peer propagation, lattice arrangements in general, etc.), collective in general, and combination thereof.

It is noted that the functional blocks and modules in FIGS. 1-6 may comprise at least one of: processors, electronics devices, hardware devices, electronics components, logical circuits, memories, software codes, firmware codes, etc., or any combination thereof.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the disclosure herein may be implemented or performed with one or more processing unit—comprising at least one of: central processing unit (CPU), graphics processing unit (GPU), digital signal processor (DSP), quantum circuit, custom designed and fabricated application specific integrated circuit (ASIC), field programmable gate array (FPGA), vision processing unit (VPU), tensor processing unit (TPU), and combination thereof—and other computer components utilized in mobile and/or stationary devices. An AI (e.g., ANN) may have access to non-volatile memory for storing, logging, troubleshooting, and the like. Input and output capabilities of an AI (e.g., ANN) may be supplemented by related input-output channels and devices. Instructions for an AI (e.g., ANN) to initialize, learn, validate, and/or infer may be delivered through one or more input channels. The execution of the commands may occur over the one or more processing units in coordination with RAM (random access memory) and storage to generate and deliver output over one or more output channels.

The invention claimed is:

1. A system for communitywide care, wherein the system is of a basis comprising intelligent awareness, and wherein the communitywide care is related to real-time remote monitoring for at least one event of one or more domain, the system comprising:
at least one processor configured to:
receive one or more first observation regarding the one or more domain;
normalize the received one or more first observation;
generate, based on the normalized one or more first observation, one or more first awareness regarding the at least one event;
receive one or more second observation regarding the one or more domain;
normalize the received one or more second observation;
generate, by executing one or more artificial intelligence (AI) construction, based on the normalized one or more second observation, one or more second awareness regarding the at least one event,
wherein one or more functional performance measure (FPM) is configured on the one or more AI construction,
and wherein the one or more FPM is regarding the communitywide care;
compare the one or more first awareness against one or more second administrator's one or more expectation;
evaluate, based on the one or more FPM and comparing the one or more first awareness against the one or more second administrator's one or more expectation, one or more first metric;
compare the one or more second awareness against one or more third administrator's one or more expectation; and
automatically evaluate, by executing the one or more AI construction, based on:
the one or more first metric,
the one or more FPM, and
comparing the one or more second awareness against the one or more third administrator's one or more expectation,
one or more second metric;
wherein the automatically evaluating enables for the communitywide care one or more improvement of a basis: prediction accuracy, or new quantification technique construction, or defect mitigation, or operation tuning, or combination thereof.

2. The system of claim 1, wherein the at least one processor is further configured to:
improve, based on the evaluated one or more second metric, prediction accuracy.

3. The system of claim 1, wherein the at least one processor is further configured to:
improve, based on the evaluated one or more second metric, new quantification technique construction.

4. The system of claim 1, wherein the at least one processor is further configured to:
improve, based on the evaluated one or more second metric, defect mitigation.

5. The system of claim 1, wherein the at least one processor is further configured to:
improve, based on the evaluated one or more second metric, operation tuning.

6. The system of claim 1, wherein the at least one processor is further configured to:
scale up, based on the automatically evaluating, the real-time remote monitoring by a ratio at least one order of magnitude greater than the ratio of a practical scale up of corresponding manual monitoring.

7. The system of claim 1, wherein the at least one processor is further configured to:
scale up, based on the automatically evaluating, the communitywide care by a ratio at least one order of magnitude greater than the ratio of a practical scale up of corresponding manual care services.

8. The system of claim 1, further comprising:
one or more computer implementation comprising the evaluated one or more second metric; and
one or more communitywide care based on the one or more computer implementation.

9. The system of claim 1, further comprising:
one or more computer implementation comprising the evaluated one or more second metric;
one or more vehicle operation based on the one or more computer implementation; and
one or more communitywide care comprising the one or more vehicle operation.

10. The system of claim 1, further comprising:
one or more computer implementation comprising the evaluated one or more second metric; and
one or more healthcare service based on the one or more computer implementation.

11. The system of claim 1, wherein the at least one processor is further configured to:
mitigate, based on the automatically evaluating, one or more tradeoff among: minimal data inundation, optimal data resolution, and optimal sampling continuity.

12. The system of claim 1, wherein the at least one processor is further configured to improve:
performance of the communitywide care related to one or more measure of a basis efficacy;
or viability of the communitywide care related to one or more measure of a basis: economic, or social, or scientific, or business, or environmental, or combination thereof;
or construction, based on improvement for the one or more FPM, of one or more subsequent second FPM;
or combination thereof.

13. The system of claim 1, wherein the at least one processor is further configured to:
update, based on the automatically evaluating, the one or more AI construction; and
improve, based on the updated one or more AI construction, the one or more FPM.

14. The system of claim 1, wherein the at least one processor is further configured to:
update, based on the automatically evaluating, the one or more AI construction; and
construct, based on the updated one or more AI construction, one or more subsequent improved second FPM.

15. The system of claim 1, wherein the at least one processor is further configured to:
update, based on the automatically evaluating, the one or more AI construction; and
formulate, based on the updated one or more AI construction, one or more third metric, wherein an evaluation of the one or more third metric represents one or more improved match with one or more administrator's one or more expectation.

16. The system of claim 1, wherein the one or more AI construction is based on neural networks.

17. The system of claim 1, wherein one series of time durations of automatically evaluating the one or more second metric is continuous, and a first individual time duration of the one series is consistent with a second individual time duration of the one series;
wherein the consistency and the continuity enable mitigation of tradeoff between data resolution and sampling continuity.

18. The system of claim 1, wherein two or more series of time durations of automatically evaluating the one or more second metric are continuous, and a first individual time duration of the two or more series is consistent with a second individual time duration of the two or more series;
wherein the consistency and the continuity enable mitigation of tradeoff between data resolution and sampling continuity.

19. The system of claim 1, wherein the automatically evaluating further comprises prioritizing, by one or more layer of the one or more AI construction, one or more correlation among: the at least one event, the one or more first metric, the one or more second administrator's one or more expectation, the one or more third administrator's one or more expectation, the one or more first awareness, and the one or more second awareness; and
wherein the automatically evaluated second metric indicates the prioritized one or more correlation.

20. A system for quantifying, the system comprising:
one or more artificial intelligence (AI) construction configured on at least one processor;
one or more functional performance measure (FPM) configured on the one or more AI construction, wherein the one or more FPM is of a plurality of business components as a whole;
and the at least one processor further configured to:
receive one or more first observation regarding one or more domain;
normalize the received one or more first observation;
generate, by executing the one or more AI construction, based on the normalized one or more first observation, one or more first awareness;
compare the one or more first awareness against one or more administrator's one or more expectation; and
automatically formulate, by executing the one or more AI construction, based on the one or more FPM and comparing the one or more first awareness against the one or more administrator's one or more expectation, one or more metric,
wherein the automatically formulating comprises incorporating the one or more expectation into the one or more metric;
wherein the automatically formulating enables:
improvement of a basis: prediction accuracy, or new quantification technique construction,
or combination thereof;
or improvement to the one or more AI construction;
or combination thereof.

21. The system of claim 20, wherein the at least one processor is further configured to:
improve, based on the automatically formulated one or more metric, one or more efficacy of a basis: prediction accuracy, or new quantification technique construction, or combination thereof.

22. The system of claim 20, wherein the at least one processor is further configured to:
update, based on automatically formulating the one or more metric, the one or more AI construction, wherein the updated one or more AI construction represents one or more improved match with the one or more administrator's one or more expectation.

23. The system of claim 20, wherein the at least one processor is further configured to:
update, based on automatically formulating the one or more metric, the one or more AI construction, wherein the updated one or more AI construction represents one or more improved match with the one or more administrator's one or more expectation;
improve, based on the updated one or more AI construction, one or more efficacy of a basis: prediction accuracy, or new quantification technique construction, or combination thereof.

24. The system of claim 20, wherein the at least one processor is further configured to:
automatically hypothesize, based on automatically formulating the one or more metric, one or more third metric.

25. The system of claim 20, wherein the at least one processor is further configured to:
automatically designate, based on automatically formulating the one or more metric, one or more third metric as axiomatic.

26. The system of claim 20, wherein the at least one processor is further configured to:
scale up, based on the automatically formulating, the quantifying by a ratio at least one order of magnitude greater than the ratio of a practical scale up of corresponding manual quantifying.

27. The system of claim 20, wherein the plurality of business components comprises three or more distinct components interacting in real-time.

28. The system of claim 20, wherein the plurality of business components comprises three or more distinct components interacting iteratively, wherein the interaction frequency is at least once per minute.

29. A system for defect mitigation, the system comprising:
one or more artificial intelligence (AI) construction configured on at least one processor,
the one or more AI construction comprising one or more generating metric regarding one or more functional performance measure (FPM),
and the at least one processor further configured to:
receive one or more first observation;
normalize the one or more first observation;
generate, by executing the one or more AI construction, based on:
the normalized one or more first observation,
the one or more generating metric, and
the one or more FPM,
one or more first awareness;
automatically compare, by executing the one or more AI construction, based on one or more comparing metric, the one or more first awareness against one or more evaluation of the one or more AI construction;
automatically detect, by executing the one or more AI construction, based on the comparing, one or more feature regarding one or more defect; and
automatically update, by executing the one or more AI construction, based on the automatically detecting, the one or more generating metric, or the one or more comparing metric, or combination thereof with the one or more feature;
wherein the automatically updating enables:
improvement of a basis: prediction accuracy, or mitigating defects, or combination thereof;
or improvement to the one or more AI construction;
or combination thereof.

30. The system of claim 29, wherein the automatically comparing, the automatically detecting, and the automatically updating occur in real-time.

31. The system of claim 29, wherein the at least one processor is further configured to:
scale up, based on the automatically comparing, the automatically detecting, and the automatically updating, the defect mitigation by a ratio at least one order of magnitude greater than the ratio of a practical scale up of corresponding manual defect mitigation.

32. The system of claim 29, wherein the at least one processor is further configured to:
improve, based on:
the automatically updated one or more generating metric,
or the automatically updated one or more comparing metric,
or combination thereof,
one or more efficacy of a basis: prediction accuracy, or mitigating defects, or combination thereof.

33. The system of claim 29, wherein a time duration spanning the automatically comparing, the automatically detecting, and the automatically updating is at least one order of magnitude less than a practical time duration needed for corresponding manual detection and corresponding manual mitigation of the one or more defect.

34. The system of claim 29, wherein the at least one processor is further configured to automatically administer, by executing the one or more AI construction,
the automatically updated one or more generating metric to overcome one or more first defect with respect to generating the one or more first awareness,
or the automatically updated one or more comparing metric to overcome one or more second defect with respect to the automatically comparing,
or the automatically updated one or more generating metric and the automatically updated one or more comparing metric to overcome one or more third defect with respect to generating the one or more first awareness and the automatically comparing.

35. A system for operation tuning, the system comprising:
one or more artificial intelligence (AI) construction configured on at least one processor, the one or more AI construction comprising one or more metric regarding one or more functional performance measure (FPM), and the at least one processor further configured to:

receive one or more first observation regarding one or more operation;

normalize the one or more first observation;

generate, by executing the one or more AI construction, based on:

the normalized one or more first observation, the one or more metric, and the one or more FPM, one or more first awareness;

automatically identify, by executing the one or more AI construction, one or more discrepancy regarding the one or more first awareness;

automatically detect, by executing the one or more AI construction, based on automatically identifying the one or more discrepancy, one or more feature regarding one or more nuance; and automatically update, by executing the one or more AI construction, based on the automatically detecting, the one or more metric with the one or more feature;

wherein the automatically updating enables:

improvement of a basis: prediction accuracy, or operation tuning, or combination thereof;

or improvement to the one or more AI construction;

or combination thereof.

36. The system of claim 35, wherein the at least one processor is further configured to:

tune, based on the automatically updated one or more metric, the one or more operation.

37. The system of claim 35, wherein the one or more nuance is based on one or more redundancy, and the at least one processor is further configured to:

mitigate, based on the automatically updated one or more metric, the one or more redundancy; and tune, based on mitigating the one or more redundancy, the one or more operation.

38. The system of claim 35, wherein the one or more nuance is based on one or more redundancy, and the at least one processor is further configured to:

mitigate, based on the automatically updated one or more metric, the one or more redundancy; and tune, based on mitigating the one or more redundancy, the one or more operation;

wherein mitigating the one or more redundancy comprises reducing one or more dimension of the one or more metric.

39. The system of claim 35, wherein the one or more nuance is based on one or more confounder, and the at least one processor is further configured to:

mitigate, based on the automatically updated one or more metric, the one or more confounder; and tune, based on mitigating the one or more confounder, the one or more operation.

40. The system of claim 35, wherein the one or more nuance is based on one or more confounder, and the at least one processor is further configured to:

mitigate, based on the automatically updated one or more metric, the one or more confounder; and tune, based on mitigating the one or more confounder, the one or more operation;

wherein mitigating the one or more confounder comprises increasing one or more dimension of the one or more metric.

41. The system of claim 35, wherein the automatically identifying, the automatically detecting, and the automatically updating occur in real-time.

42. The system of claim 35, wherein a time duration spanning the automatically identifying, the automatically detecting, and the automatically updating is at least one order of magnitude less than a practical time duration needed for corresponding manual detection of the one or more nuance and corresponding manual update of the one or more metric.

43. The system of claim 35, wherein the at least one processor is further configured to:

tune, based on the automatically updated one or more metric, the one or more operation; and scale up, based on the automatically identifying, the automatically detecting, and the automatically updating, tuning the one or more operation by a ratio at least one order of magnitude greater than the ratio of a practical scale up of corresponding manual tuning.

44. The system of claim 1, wherein the one or more second metric is based on sixteen or more elements.

45. The system of claim 1, wherein the one or more second metric is based on four or more dimensions.

46. The system of claim 1, wherein the at least one processor is further configured to:

regulate with respect to one or more specification, based on normalizing the one or more second observation, automatically evaluating the one or more second metric.

47. The system of claim 1, wherein the at least one processor is further configured to:

regulate with respect to one or more expectation, based on normalizing the one or more second observation, comparing the one or more second awareness against the one or more third administrator's one or more expectation.

* * * * *